United States Patent

Murad et al.

Patent Number: 5,478,946
Date of Patent: Dec. 26, 1995

[54] GUANIDINO COMPOUNDS AS REGULATORS OF NITRIC OXIDE SYNTHASE

[75] Inventors: Ferid Murad, Lake Forest; James F. Kerwin, Grayslake; Lee D. Gorsky, Highland Park, all of Ill.

[73] Assignee: Abbott Laboratories, Abbott Park, Ill.

[21] Appl. No.: 159,409

[22] Filed: Nov. 30, 1993

Related U.S. Application Data

[63] Continuation-in-part of Ser. No. 755,398, Sep. 5, 1991, Pat. No. 5,288,897, which is a continuation-in-part of Ser. No. 369,364, Jun. 21, 1989, abandoned.

[51] Int. Cl.$^6$ .................................................. C07D 263/02
[52] U.S. Cl. .................... 548/215; 548/567; 560/34; 564/108; 564/104; 564/226; 564/227; 564/229
[58] Field of Search ...................... 548/215, 567; 560/34; 564/108, 104, 226, 227

[56] References Cited

U.S. PATENT DOCUMENTS 4,677,226  6/1987  Lutz et al. ............................ 564/108
5,296,498  3/1994  Molen et al. ......................... 564/401

Primary Examiner—Paul J. Killos
Attorney, Agent, or Firm—Richard A. Elder; Steven R. Crowley; Steven F. Weinstock

[57] ABSTRACT

Compounds of the formula:

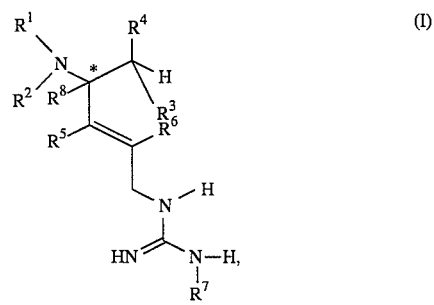

useful as regulators of nitric oxide synthase that indirectly modulate cyclic guanosine monophosphate (cGMP), pharmaceutical compositions thereof, for treating disorders of vascular smooth muscles, macrophages, neurons, platelets, bronchial smooth muscles, optic muscles and gastrointestinal smooth muscles, sickle cell anemia and diabetes.

8 Claims, No Drawings

GUANIDINO COMPOUNDS AS REGULATORS OF NITRIC OXIDE SYNTHASE

CROSS REFERENCE TO RELATED APPLICATIONS

This application is a continuation-in-part of allowed U.S. Pat. application Ser. No. 07/755,398, filed Sep. 5, 1991, now U.S. Pat. No. 5,288,897 which is a continuation-in-part of U.S. Pat. application Ser. No. 07/369,364, filed Jun. 21, 1989, now abandoned.

TECHNICAL FIELD

The present invention relates to novel unsaturated guanidino compounds, to compositions thereof useful in regulating the production of soluble guanylate cyclase or nitric oxide, to intermediates useful in the production thereof, and to a method of treating disorders of the vascular system or diseases of the cartilage, including hypotension, hypertension, coronary vasospasm, cerebral vasoconstriction, cardiomyopathy, atherogenesis, atherosclerosis, myocardial ischemia, cerebral ischemia, diabetes, endotoxemia, sepsis, asthma and rhinitis, synovitis, chondroarthdtis and osteoarthritis.

BACKGROUND OF THE INVENTION

Furchgott (*Nature*, 1980, 288:373–6) reported in 1980 that endothelial cells release a powerful vasodilator which is termed endothelium-derived relaxing factor (EDRF). Subsequent research has shown that many endothelium-dependent receptor agonists, including, for example, adenosine diphosphate (ADP), adenosine triphosphate (ATP), 5-hydroxytryptamine (5-HT), thrombin, acetylcholine (ACh), vasoactive intestinal polypeptide (VIP), oxytocin, cholecystokinin (CCK), calcitonin gene-related peptide, noradrenaline, histamine, calcium ionophores, melittin and ergometrine invoke the release of EDRF. The release of EDRF, in turn, stimulates the soluble form of the enzyme guanylate cyclase, thereby increasing levels of the second messenger, cyclic guanosine monophosphate (cGMP), which, in turn, produces vasorelaxation. Reviews are available which discuss this process in more detail (see, for example, A. M. Katz, *J. Am. Coll. Cardiol.*, 1988, 12: 797–806; J. A. Angus and T. M. Cocks, *Pharmaceutical Therapeutics*, 1989, 41:303–52; S. A. Waldman and F. Murad, *Pharmacological Reviews*, 1987, 39:163–196; F. Murad, *J. Clin. Invest.*, 1986, 75: 1–5; L. J. Ignarro, *Biochem. Pharmacol.*, 1991,41: 485–90; and S. Moncada, R. M. J. Palmer and E. A. Higgs, *Pharmacological Reviews*, 1991, 43: 109–142).

Pharmacological characterization of EDRF and its effects has been an active area of research over the past eleven years (K. Shikano et al., *J. Pharmaco. Expo Therap.*, 1988, 247:873–81 and L. J. Ignarro, *Annu. Rev. Pharmaco. Toxicol.*, 1990, 30: 535–60), and now there is substantial evidence that nitric oxide (NO) is the major endothelium-derived relaxing factor (R. M. J. Palmer et al., *Nature*, 1987, 327: 524–6; S. Moncada et al., *Biochem. Pharmacol.*, 1989, 38: 1709–15; and S. Moncada et al., *Hypertension*, 1989, 12: 365–72). In particular, nitric oxide (NO) was tested and found to elicit a potent and transient relaxation of bovine coronary artery accompanied by cGMP accumulation (C. A. Guetter et al, *J. Cyclic Nucleotide Res.*, 1979, 5:211–24) and it was also shown to activate soluble guanylate cyclase and to elevate tissue cGMP levels.

Recent reports (H. H. H. W. Schmidt et al., *European J. Pharmacol.*, 1988, 154:213–6 and S. Moncada et al., *Hypertension*, 1988, 12: 365–72) have suggested that L-arginine may be the endogenous source of EDRF (NO), and this hypothesis is further supported by the observation that EDRF (NO) production is inhibited by the simple arginine derivative, $N^G$-methylarginine (R. M. J. Palmer et al., *Biochem. Biophys. Res. Comm.*, 1988, 153: 1251–56; S. Moncada et al., *Biochemical Pharmacology*, 1988, 37: 2495–2501; and I. Sakuma et al., *Proc. Natl. Acad. Sci. USA*, 1988, 85: 8664–7).

Increasing evidence has been uncovered that suggests EDRF or EDRF-like substances may also control cGMP production in non-endothelial cells (J. Garthwaite, *Nature*, 1988, 336:385–388 and T. J. Rimele et al., *J. Pharmacol. Exp. Therap.*, 1988, 245:102–111) and that this method of guanylate cyclase regulation may be ubiquitous. A role in the regulation of neural transmission and a role in the neural control of gastrointestinal smooth muscle function has been elucidated (J. Collier and P. Vallance, *Trends in Pharmacological Sciences*, 1989, 428–31 and K. M. Desai et al., *Nature*, 1991, 351: 477–9). Compounds that control, inhibit, or otherwise regulate this pathway, therefore, have potentially many and varied therapeutic applications, for instance, as analgesics (Duarte et al., *European J. Pharmacology*, 1990, 1486: 289–93), as cerebroprotectives (cf. Southham et al., *J. Neurochem.*, 1991,56: 2072–81) and as hypocholesteremics (Cooke et al., *Circulation*, 1991,83:1057–62).

Recent work has shown that there are many isoforms of the EDRF (NO) synthase enzyme. The primary distinction among these isoforms is whether they are constitutive or inducible forms, but other factors which serve to distinguish these isoforms are their cellular localization and their cofactor requirements. Many of these isoforms have been arbitrarily given Roman numeral designations and are described in the table below, wherein NADPH represents reduced nicotinamide adenine dinucleotide phosphate, $BH_4$ represents tetrahydrobiopterin, FAD represents flavin adenine dinucleotide and FMN represents flavin mononucleotide.

| Type | Cosubstrates & Cofactors | Regulated by | $M_r$ of denatured protein* | Present in |
|---|---|---|---|---|
| I (soluble) | NADPH, $BH_4$ | $Ca++$, calmodulin | 155 kDa** | brain and cerebellum |
| II (soluble) | NADPH, $BH_4$, FAD/FMN, thiols, $Mg++$ | induced by endotoxin and cytokines | 125–135 kDa** | macrophages |
| III | NADPH | $Ca++$, | 135 kDa** | endothelial |

-continued

| Type | Cosubstrates & Cofactors | Regulated by | $M_r$ of denatured protein* | Present in |
|---|---|---|---|---|
| (particulate) | $BH_4$ | calmodulin | | cells |

*Molecular weight determination by sodium dodecyl sulfate/polyacrylamide gel electrophoresis
**kiloDaltons Isoform I has been purified and characterized by Bredt and Snyder (*Proc. Natl. Acad. Sci. USA*, 1989, 87: 682–685) and by Schmidt et al. (*Proc. Natl. Acad. Sci. USA*, 1989, 88: 365–369). Isoform II has been purified and characterized by Kawai et al. (*J. Biological Chemistry*, 1991,266: 12544–47). Isoform III has been purified and characterized by Pollock et al. (*Proc. Natl. Acad. Sci. USA*, 1991, 88: 10480-4). Isoform-specific agents may offer the advantage of selectivity, i.e., desired therapeutic effect with fewer or more tolerable side effects.

Compounds which act directly to regulate NO synthesis or in an indirect fashion to regulate the production of cGMP through regulation of the effect of endogenous EDRF (NO) on soluble guanylate cyclase are useful in the treatment of those disease states associated with smooth muscle and smooth muscle tone, especially those involving airway, gastrointestinal and vascular muscle, and platelet function. Examples of such conditions include hypotension, endotoxemia, shock, sepsis, rhinitis, hypertension, and cerebral vasoconstriction and vasodilation, such as migraine and non-migraine headache, ischemia, thrombosis, and platelet aggregation, including preservation and processing of platelets for transfusions and perfusion technologies. Additional examples include atherosclerosis, diseases of the bronchial passages, such as asthma, diseases of the optic musculature, diseases of the gastrointestinal system, such as reflux esophagitis (GERD), spasm, diarrhea, irritable bowel syndrome, and other gastrointestinal motile dysfunctions. Such compounds may also find use in angioplasty and the treatment of sickle cell anemia.

Examples of known compounds that act to regulate the production of cGMP by this method may be grouped into four categories: (1) those compounds, for example, methylene blue, which directly or indirectly (through superoxide anion) oxidize EDRF (NO) and thereby inactivate it (R. J. Gryglewski et al., *Nature*, 1986, 320:454–6 and S. Moncada et al., *Proc. Natl. Acad. Sci. USA*, 1986, 83: 9164–68); (2) those agents, for example, hemoglobin, which directly bind either EDRF (NO) itself or one of its end products; (3) those agents which remove superoxide anion ($O_2$)— and other oxidants, thereby enhancing the effect of EDRF (for example, the enzyme superoxide dismutase removes superoxide anion by converting it to molecular oxygen ($O_2$) and hydrogen peroxide); and (4) the nitrovasodilators, such as nitroglycerin, which provide nitrogen oxide to stimulate guanylate cyclase (F. Murad, *J. Clin. Invest.*, 1986, 78: 1–5). With the exception of the nitrovasodilators, none of these categories of compounds has provided a viable therapeutic agent for the regulation of cGMP production in disease states. The nitrovasodilators, because they provide nitrogenous oxides indiscriminately to numerous target tissues, and thus lead to such complications as tolerance (A. Mulsch et al., *European J. Pharmacol.*, 1988, 158: 191–8), may not be the ultimate therapeutic agents of choice. More recently it has been reported that N-hydroxyarginine is a substrate for the NO synthase enzyme (Steuhr et al., *J. Biol. Chem.*, 1991, 266:6259 ).

SUMMARY OF THE INVENTION

The present invention is directed to regulators of nitric oxide synthase that indirectly modulate cyclic guanosine monophosphate (cGMP) production which have the formula:

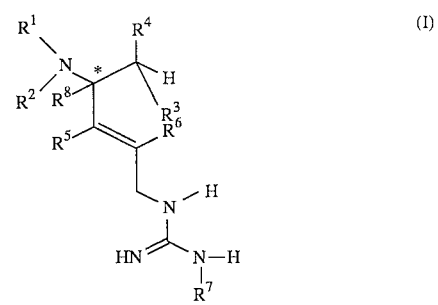

or a pharmaceutically-acceptable salt, ester, amide or pro-drug thereof.

The present invention is also directed to pharmaceutical compositions comprising a therapeutically-effective amount of a compound of formula (I) and a pharmaceutically-acceptable carder or diluent, and to a method of treating disorders of vascular smooth muscles, macrophages, neurons, platelets, bronchial smooth muscles, optic muscles and gastrointestinal smooth muscles in humans and mammals, in addition to sickle cell anemia and diabetes, by administration of a compound of formula (I).

DETAILED DESCRIPTION OF THE INVENTION

This invention relates to novel unsaturated guanidino compounds and pharmaceutical compositions thereof which regulate nitric oxide synthase and thereby indirectly modulate levels of cyclic guanosine monophosphate. These compounds may, therefore, be used in the treatment of disorders of vascular smooth musculature, macrophages or neurons, such as hypotension, endotoxemia, sepsis, hypertension, shock, cerebral vasoconstriction, cerebral vasodilation, or headache; in disease states involving platelet aggregation, including preparation of platelets for transfusion; in angioplasty, ischemia, thrombosis, coronary vasospasm, cardiomyopathy, atherogenesis, atherosclerosis, sickle cell anemia and diabetes; in diseases involving the bronchial passages such as asthma; in diseases of the optic musculature; and in diseases of the gastrointestinal system, such as diarrhea, irritable bowel syndrome, spasm, and esophagitis (GERD).

In particular, the invention is directed to compounds of formula (I):

$$\text{(I)}$$

or a pharmaceutically-acceptable salt, ester, amide or prodrug thereof, wherein:

* represents a potential chiral center;

$R^1$ is selected from the group consisting of:
(1) hydrogen;
(2) $C_1$–$C_6$-alkyl;
(3) $C_6$–$C_{12}$-aryl-$C_1$–$C_4$-alkyl, as defined below;
(4) substituted $C_6$–$C_{12}$-aryl-$C_1$–$C_4$-alkyl, as defined below;
(5) N-protecting group, as defined below;
(6) —CO—$C_1$–$C_6$-alkyl;
(7) —CO—$C_6$–$C_{12}$-aryl, wherein $C_6$–$C_{12}$-aryl is as defined below;
(8) —CO—substituted $C_6$–$C_{12}$-aryl, wherein substituted $C_6$–$C_{12}$-aryl is as defined below;
(9) —CO—($C_6$–$C_{12}$-aryl-$C_1$–$C_4$-alkyl);
(10) —CO—(substituted $C_6$–$C_{12}$-aryl-$C_1$–$C_4$-alkyl); and
(11) —CO—Het, wherein Het is as defined below;

$R^2$ is selected from the group consisting of:
(1) hydrogen;
(2) $C_1$–$C_6$-alkyl;
(3) $C_6$–$C_{12}$-aryl-$C_1$–$C_4$-alkyl; and
(4) substituted $C_6$–$C_{12}$-aryl-$C_1$–$C_4$-alkyl;

$R^3$ is selected from the group consisting of:
(1) hydrogen;
(2) $C_1$–$C_6$-alkyl;
(3) $C_2$–$C_6$-alkenyl, as defined below;
(4) cyclo-$C_3$–$C_7$-alkyl, as defined below;
(5) $C_6$–$C_{12}$-aryl; and
(6) substituted $C_6$–$C_{12}$-aryl;

$R^4$ is selected from the group consisting of:
(1) hydroxy;
(2) $C_1$–$C_6$-alkoxy, as defined below;
(3) $C_6$–$C_{12}$-aryloxy, as defined below;
(4) substituted $C_6$–$C_{12}$-aryloxy, as defined below;
(5) —O—($C_1$–$C_6$-alkyl-$C_6$–$C_{12}$-aryl);
(6) —O—(substituted $C_6$–$C_{12}$-aryl-$C_1$–$C_4$-alkyl); and
(7) —NHR$^{11}$, wherein R$^{11}$ is hydrogen or $C_1$–$C_4$-alkyl;

or $R^2$ and $R^4$ are linked together by a single bond to form a nitrogen-containing ring of the formula:

wherein $R^1$ and $R^3$ are as defined above, $R^4$ is O and $R^2$ is —CR$^9$R$^{10}$, is selected from the group consisting of:
(1) hydrogen;
(2) $C_1$–$C_6$-alkyl;
(3) substituted $C_1$–$C_6$-alkyl, as defined below;
(4) $C_6$–$C_{12}$-aryl;
(5) substituted $C_6$–$C_{12}$-aryl;
(6) $C_2$–$C_6$-alkenyl;
(7) carboxy;
(8) $C_1$–$C_4$-alkoxycarbonyl, as defined below;
(9) carboxamido; and
(10) cyano;

$R^{10}$ is hydrogen or $C_1$–$C_6$-alkyl; and $R^{12}$ is hydrogen or $C_1$–$C_4$-alkyl;

$R^5$ and $R^6$ are independently selected from the group consisting of:
(1) hydrogen;
(2) $C_1$–$C_4$-alkyl;
(3) $C_6$–$C_{12}$-aryl-$C_1$–$C_6$-alkyl;
(4) substituted $C_6$–$C_{12}$-aryl-$C_1$–$C_6$-alkyl;
(5) halo-$C_1$–$C_2$-alkyl, as defined below; and
(6) halogen;

$R^7$ is selected from the group consisting of:
(1) hydrogen;
(2) $C_1$–$C_3$-alkyl;
(3) cyano;
(4) nitro;
(5) hydroxy;
(6) amino; and
(7) —OR$^{15}$, wherein R$^{15}$ is a hydroxy-protecting group, as defined below; and $R^8$ is hydrogen or $C_1$–$C_4$-alkyl.

When a variable or substituent occurs more than once in any structure, it is understood to be independently selected at each occurrence.

One embodiment of the present invention comprises compounds represented by the formula:

wherein B is $$\text{(1a)}$$

wherein $R^1$, $R^3$, $R^5$, $R^6$, and $R^7$ are as defined above, and $R^2$ and $R^4$ are linked together as defined above; or $$\text{(1b)}$$

wherein $R^1$, $R^2$, $R^3$, $R^5$, $R^6$, $R^7$, and $R^8$ are as defined above.

A preferred embodiment of the above compound is one wherein $R^5$ and $R^6$ are hydrogen and the chiral center is S.

Representative of the compounds of the invention are:

$N^G$-Nitroguanidinyl-4(S)-amino-pent-2,E-ene-5-ol;

3-(1,1-Dimethylethyl)-(S)-4-(3-guanidinopropen-1, E-yl)-2,2-dimethyl-3-oxazolidinecarboxylate;

1-Guanidinyl-4(S)-amino-pent-2,E-ene-5-ol;

$N^G$-Aminoguanidinyl-4(S)-amimo-pent-2,E-ene-5-ol;

3-(1,1 -Dimethylethyl)-(S)-4-(3-$N^G$-hydroxyguanidinopropen-1,E-yl)-2,2-dimethyl-3 -oxazolidinecarboxylate;

$N^G$-Hydroxyguanidinyl-4(S)-amino-pent-2,E-ene-5-ol;

3-(1,1-Dimethylethyl)-(S)-4-(3-$N^G$-methylguanidinopropen-1,E-yl)-2,2-dimethyl-3 -oxazolidinecarboxylate;

$N^G$-Methylguanidinyl-4(S)-amino-pent-2,E-ene-5-ol;

3-(1,1 -Dimethylethyl)-(S)-4-(3-$N^G$-ethylguanidinopropen-1,E-yl)-2,2-dimethyl-3 -oxazolidinecarboxylate;

$N^G$-Ethylguanidinyl-4(S)-amino-pent-2,E-ene-5-ol;

$N^4$-Boc-$N^G$-Nitroguanidinyl-4(S)-amino-pent-2, E-ene-5-ol;

3-(1,1 -Dimethylethyl)-(S)-4-(3-nitmguanidino-2-methylpropen-1,E-yl)-2,2 -dimethyl-3-oxazolidinecarboxylate;

$N^G$-Nitroguanidinyl-4(S)-amino-2-methyl-pent-2,E-ene-5-ol;

$N^4$-Boc-$N^G$-Methylguanidinyl-4(S)-amino-pent-2,E-ene-5-ol;

3-(1,1 -Dimethylethyl)-(R)-4-(3-$N^G$-methylguanidinopropen-1,E-yl)-2,2-dimethyl-3-oxazolidinecarboxylate;

$N^G$-Methylguanidinyl-4(R)-amino-pent-2,E-ene-5-ol;

3-(1,1-Dimethylethyl)-(S)-4-(3-methylguanidino-2-methylpropen-1,E-yl)-2,2-dimethyl-3-oxazolidinecarboxylate;

$N^G$-Methylguanidinyl-4(S)-amino-2-methyl-pent-2,E-ene-5-ol;

3-(1,1 -Dimethylethyl)-(R )-4-(3-guanidinopropen- 1 ,E-yl)-2,2-dimethyl-3 -oxazolidinecarboxylate;

3-(1,1-Dimethylethyl)-(S)-4-(3-guanidino-2-benzyl-propen-1 ,E-yl)-2,2-dimethyl-3 -oxazolidinecarboxylate;

$N^G$-Guanidinyl-4(S)-amino-2-benzyl-pent-2,E-ene-5-ol;

$N^G$-Methylguanidinyl-4(S)-Amino-2-methyl-pent-2,E-ene-5-ol; and 3-(1,1 -Dimethylethyl)-(S)-4-(3-$N^G$-propylguanidino-2-methyl-propen-1 ,E-yl)-2,2 -dimethyl-3-oxazolidinecarboxylate.

Illustrative of the preferred compounds of the invention are:

$N^G$-Nitroguanidinyl-4(S)-amino-pent-2,E-ene-5-ol;

$N^G$-Methylguanidinyl-4(S)-amino-pent-2,E-ene-5-ol;

$N^G$-Nitroguanidinyl-4(S)-amino-2-methyl-pent-2,E-ene-5-ol;

$N^G$-Guanidinyl-4(S)-amino-2-methyl-pent-2,E-ene-5-ol; and $N^G$-Methylguanidinyl-4(S)-amino-2-methyl-pent-2,E-ene-5-ol.

"$C_2$–$C_6$-Alkenyl" refers to a straight or branched chain radical from 2-to-6 carbon atoms, which contains at least one carbon-carbon double bond.

"Alkoxy", refers to $R^{19}$O—, wherein $R^{19}$ is either a $C_1$–$C_4$- or a $C_1$–$C_6$-alkyl group, as specified.

"Alkoxycarbonyl" refers to $A^2$O—C(O)—, wherein $A^2$ is a $C_1$–$C_4$-alkyl group, and includes, for example, methoxycarbonyl, ethoxycarbonyl, n-propyloxycarbonyl, isopropyloxycarbonyl, n-butyloxycarbonyl, isobutyloxycarbonyl and t-butyloxycarbonyl.

"Alkyl" refers to straight- or branched-chain alkyl radicals containing from 1-to-3 carbon atoms ("$C_1$–$C_3$-alkyl"), 1-to-4 carbon atoms ("$C_1$–$C_4$-alkyl") or from 1-to 6 carbon atoms ($C_1$–$C_6$-alkyl) including, but not limited, to methyl, ethyl, n-propyl, isopropyl, n-butyl, isobutyl, sec-butyl, n-pentyl, 2-methylbutyl, 2,2-dimethylpropyl, n-hexyl, 2-methylpentyl, 2,2-dimethylbutyl, n-hexyl, and the like.

"$C_6$–$C_{12}$-Aryl" or "$C_6$–$C_{12}$-aryl group", as used herein, refers to carbocyclic aromatic isolated or fused rings of from 6-to-12 carbon atoms, for example, phenyl, naphthyl, indanyl, fluorenyl, terahydronaphthyl, indenyl, or isoindenyl.

"$C_6$–$C_{12}$-Aryl-$C_1$–$C_4$-alkyl" refers to a $C_6$–$C_{12}$-aryl group, as defined above, appended to a $C_1$–$C_4$-alkyl radical, as defined above, including, but not limited to, benzyl, phenylethyl, naphthylmethyl, and the like.

"$C_6$–$C_{12}$-Aryloxy" refers to $R^{22}$O—, wherein $R^{22}$ is an $C_6$–$C_{12}$-aryl group, as defined above.

"Cyclo-$C_3$–$C_7$-alkyl" refers to an alicyclic saturated ring having from 3-to-7 carbon atoms, including but not limited to, cyclopropyl, cyclobutyl, cyclopentyl, cyclohexyl, and the like.

"Halogen" refers to fluoro (F), chloro (CI), bromo (Br) and iodo (I).

"Halo-$C_1$–$C_2$-alkyl" refers to a $C_1$–$C_4$-alkyl radical, as defined above, in which one to three hydrogen atoms have been replaced by a halogen, including, but not limited to, chloromethyl, 2-fluoroethyl, trifluoromethyl, and the like.

"Het", as used herein, refers to aromatic or fused aromatic rings of from 2 to 11 carbon atoms and from 1-to-3 heteroatoms independently selected from the group consisting of nitrogen, oxygen and sulfur. Representative Het compounds include, but are not limited to, pyrrolyl, pyridyl, indolyl, quinolinyl, benzimidazolyl, furyl, thienyl, benzothienyl, pyrazolyl, pyrazidinyl, isoquinolinyl, oxazolyl, isoxazolyl, thiazolyl, imidazolyl, and the like.

"Hydroxy-protecting group" or "O-protecting group" refers to a substituent which protects hydroxyl groups against undesirable reactions during synthetic procedures and includes, but is not limited to, substituted methyl ethers, for example, methoxymethyl, benzyloxymethyl, 2-methoxyethoxymethyl, 2-(trimethylsilyl)ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates.

"N-Protecting group", "nitrogen-protecting group" or "N-protected" refers to those groups intended to protect an amino group or the N-terminus of an amino acid or peptide against undesirable reactions during synthetic procedures or to prevent the attack of exopeptidases on the compounds or to increase the solubility of the compounds, and includes, but is not limited to, sulfonyl; acyl, such as acetyl, pivaloyl and benzoyl; alkoxycarbonyl, such as t-butyloxycarbonyl (Boc) and carbobenzyloxy (Cbz); and α-aminoacyl residues, which may themselves be similarly N-protected. Other intended groups may be found in Volume 3 of *The Peptides*, E. Gross and J. Meinhofer, editors, Academic Press, 1981.

"Pharmaceutically-acceptable ester" refers to the pharmaceutically-acceptable, nontoxic esters of the compounds of the present invention which include $C_1$–$C_6$-alkyl esters, wherein $C_1$–$C_6$-alkyl is as defined above, and $C_5$–$C_7$-cycloalkyl esters, wherein $C_5$–$C_7$-cycloalkyl refers to cyclic saturated hydrocarbon radicals, such as cyclopentyl, cyclohexyl, and the like. Also included are $C_6$–$C_{12}$-aryl-$C_1$–$C_6$-alkyl esters, wherein $C_6$–$C_{12}$-aryl-$C_1$–$C_6$-alkyl are as defined above. Representative examples include benzyl, phenethyl, and the like.

"Pharmaceutically-acceptable salts" refers to the pharmaceutically-acceptable, nontoxic, inorganic or organic acid addition salts of the compounds of the present invention. These salts can be prepared in situ during the final isolation and purification of the compounds, or by separately reacting the free base with a suitable organic or inorganic acid.

Representative salts include the hydrochloride, hydrobromide, sulfate, phosphate, nitrate, bisulfate, acetate, oxalate, valerate, oleate, palmitate, methanesulfonate, stearate, laurate, borate, benzoate, lactate, phosphate, tosylate citrate, maleate, fumarate, succinate, tartrate, napsylate, and the like.

"Polypeptide chain", as used herein, refers to a series of from 1-to-6 amino acids joined by amide linkages which may be branched or linear, wherein the amino acids are selected independently from naturally-occurring amino acids, including but not limited to glycine, alanine, leucine, valine, phenylalanine, proline, methionine, tryptophan, asparagine, aspartic acid, glutamic acid, glutamine, serine, threonine, lysine, arginine, tyrosine, histidine, ornithine and the like.

The term "prodrug" refers to compounds that are rapidly transformed in vivo to yield the parent compounds of Formula (I), as for example, by hydrolysis in blood. T. Higuchi and V. Stella provide a thorough discussion of the prodrug concept in *Prodrugs as Novel Delivery Systems*, Vol. 14 of the A.C.S. Symposium Series, American Chemical Society (1975). Examples of esters useful as prodrugs for compounds containing carboxyl groups can be found on pages 14– 21 of *Bioreversible Carriers in Drug Design: Theory and Appication*, edited by E. B. Roche, Pergamon Press (1987).

The term "prodrug ester group" refers to any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art.

The term "protecting group" is well known in the art and refers to sustituents on functional groups of compounds undergoing chemical transformation which prevent undesired reactions and degradations during a synthesis; see, for example, T. H. Greene, *Protective Groups in Organic Synthesis*, John Wiley & Sons, (1981).

"Substituted $C_3$–$C_4$-alkenylene" refers to alkenylene groups wherein, in each case, one of the carbon atoms in the alkenylene chain is substituted with one-or-two substituents independently selected at each occurrence from the group consisting of (i) halogen, (ii) $C_1$–$C_4$-alkyl, (iii) $C_1$–$C_2$-haloalkyl, (iv) $C_6$–$C_{12}$-aryl-$C_1$–$C_6$-alkyl, and (v) substituted $C_6$–$C_{12}$-aryl-$C_1$–$C_6$-alkyl.

"Substituted $C_6$–$C_{12}$-aryl" refers to a $C_6$–$C_{12}$-aryl group, as defined above, substituted with one, two, or three substituents independently selected from $C_1$–$C_4$-alkyl, $C_1$–$C_4$-alkoxy, $C_1$–$C_4$-thioalkoxy, carboxy, carbo-$C_1$–$C_4$-alkoxy, nitro, halo-$C_1$–$C_4$-alkyl, hydroxy, amino, and $C_1$–$C_4$-alkylamino.

"Substituted $C_6$–$C_{12}$-aryl-$C_1$–$C_4$-alkyl" refers to a $C_6$–$C_{12}$-aryl group, as defined above, appended to a $C_1$–$C_4$-alkyl radical, as defined above.

"Substituted $C_6$–$C_{12}$-aryloxy" refers to a $A^3O$— group, wherein $A^3$ is a substituted $C_6$–$C_{12}$-aryl group, as defined above.

By a "therapeutically-effective amount" of the compound of the invention is meant a sufficient amount of the compound to treat disorders, at a reasonable benefit/risk ratio applicable to any medical treatment. It will be understood, however, that the total daily usage of the compounds and compositions of the present invention is to be decided by the attending physician within the scope of sound medical judgment. The specific therapeutically-effective dose level for any particular patient will depend upon a variety of factors including the disorder being treated and the severity of the disorder; activity of the specific compound employed; the specific composition employed; the age, body weight, general health, gender and diet of the patient; the time of administration, route of administration, and rate of excretion of the specific compound employed; the duration of the treatment; drugs used in combination or coincidental with the specific compound employed; and like factors well known in the medical arts and well within the capabilities of attending physicians.

The following abbreviations are used herein: BOC or Boc for t-butyloxycarbonyl, Bz for benzyl, CBZ for benzyloxycarbonyl, $CDCl_3$ for deutemchloroform, $D_2O$ for deuterium oxide, DCC for dicyclohexylcarbodiimide, DIBAL for diisobutylaluminum hydride, DIEA for diisopropylethylamine, DMAP for dimethylaminopyridine, DMF for N,N-dimethylformamide, DMSO for dimethylsulfoxide, DMSO-$d_6$ for deuterodimethylsulfoxide, EDCI for 1-(3 -dimethylaminopropyl)-3-ethylcarbodiimide hydrochloride, EtOH for ethanol, HOAc for acetic acid, IBCF for isobutyl chloroformate, LAH for lithium aluminum hydride, Ms for methanesulfonyl, NH4OAc for ammonium acetate, NMM for N-methylmorpholine and TEA for triethylamine, PAW for pyridine/acetic acid/water (20:6:11 ), rt for room temperature, TFA for trifluoroacetate, THF for tetrahydrofuran, and TMSi for trimethylsilyl.

Amino acids are herein designated as the natural L-isomer or as the D-isomer in accordance with convention, or chiral compounds, including amino acids, are assigned the R, S, or (B,S) configuration at the chiral center. Preferred compounds of the present invention are those which have the S configuration at the alpha-carbon atom, i.e., the carbon atom in the formula (I) designated by an *. The terms "R" and "S" configuration used herein are as defined by IUPAC (IUPAC 1974 Recommendations for Section E. Fundamental Stereochemistry, *Pure Appl. Chem.*, 1976, 45: 13–30.)

The compounds of the present invention may be used in the form of pharmaceutically-acceptable salts derived from inorganic or organic acids. These salts include, but are not limited to, the following: acetate, adipate, alginate, aspartate, benzoate, benzenesulfonate, bisulfate, butyrate, camphorate, camphorsulfonate, citrate, cyclopentanepropionate, digluconate, dodecylsulfate, ethanesulfonate, flavianate, fumarate, glucoheptonate, glycerophosphate, hemisulfate, heptanoate, hexanoate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, phosphate, picrate, pivalate, propionate, succinate, tartrate, thiocyanate, tosylate, and undecanoate.

Appropriate cationic salts are also readily prepared by conventional procedures such as treating an acid of formula I with an appropriate amount of base, such as an alkali or alkaline earth metal hydroxide e.g., sodium, potassium, lithium, calcium, or magnesium, or an organic base such as an amine, e.g., dibenzylethylenediamine, cyclohexylamine, dicyclohexylamine, triethylamine, piperidine, pyrrolidine, benzylamine, and the like, or a quaternary ammonium hydroxide such as tetramethylammonium hydroxide and the like. Also, the basic nitrogen-containing groups may be quaternized with such agents as loweralkyl halides, including methyl, ethyl, propyl, and butyl chlorides, bromides, and iodides; dialkyl sulfates; long chain halides such as decyl, lauryl, mydstyl, and stearyl chlorides, bromides and iodides; arylalkyl halides like benzyl and phenethyl bromides, and others. Water or oil-soluble or dispersible products are thereby obtained.

When a compound of formula (I) is used in a human subject, the total daily dose administered in single or divided doses may be in amounts, for example, from about 0.01 to about 50 mg/kg body weight, or more usually, from about 0.2 to about 30 mg/kg body weight. Single dose compositions may contain such amounts or submultiples thereof to make up the daily dose. In general, treatment regimens according to the present invention comprise administering to a patient in need of such treatment from about 20 mg to about 2000 mg of the compound(s) of this invention per day in multiple doses or in a single dose.

The amount of active ingredient that may be combined with the carrier materials to produce a single dosage form will vary depending upon the host treated, the particular treatment and the particular mode of administration.

The compounds of the present invention may be administered orally, parenterally, by inhalation spray, rectally, or topically in dosage unit formulations containing conventional nontoxic pharmaceutically-acceptable carriers, adjuvants, and vehicles as desired. The term parenteral as used herein includes subcutaneous injections, intravenous, intramuscular, intrasternal injection, or infusion techniques.

Liquid dosage forms for oral administration may include pharmaceutically-acceptable emulsions, microemulsions, solutions, suspensions, syrups and elixirs containing inert diluents commonly used in the art such as water. Such compositions may also comprise adjuvants, such as wetting agents; emulsifying and suspending agents; and sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butandiol. Among the acceptable vehicles and solvents that may be employed are water, Ringers solution, isotonic sodium chloride solution. In addition, sterile fixed oils are conventionally employed as a solvent or suspending medium. For this purpose any bland fixed oil may be employed including synthetic mono- or diglycerides. In addition, fatty acids such as oleic acid find use in the preparation of injectables.

The injectable formulation can be sterilized, as for example by filtration through a bacteria-retaining filter, or by incorporating sterilizing agents in the form of sterile solid compositions which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include polyorthoesters and polyanhydrides. The depot injectables can also be made by entrapping the drug in liposomes or microemulsions which are compatible with body tissues.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Dosage forms for topical or transdermal administration of a compound of this invention include ointments, pastes, creams, lotions, gels, powders, solutions, sprays, inhalants or patches. The active component is admixed under sterile conditions with a pharmaceutically-acceptable carrier and any needed preservatives or buffers as may be required. Ophthalmic formulations, ear drops, eye ointments, powders and solutions are also contemplated as being within the scope of this invention.

The present agents can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic physiologically acceptable and metabolizable lipid capable of forming liposomes can be used. The present compositions in liposome form can contain, in addition to the compounds of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Vol. XIV, Academic Press, New York, N.Y. 1976, pp. 33 et seq.

The compounds of this invention may be administered alone or in combination or in concurrent therapy with other agents.

The foregoing is merely illustrative of the invention and is not intended to limit the invention to the disclosed compounds. Variations and changes which are obvious to one skilled in the art are intended to be within the scope and nature of the invention which are defined in the appended claims.

Synthesis of the Compounds of the Invention

In general compounds of the current invention may be prepared in the following ways: starting with a D, L, or D,L β-hydroxy-α-amino acid (1) (the R enantiomer at the α carbon center is shown for illustration) N-protected with a protecting group (P) of which Boc, Cbz, Fmoc, etc. are preferred, an ester (2), where R=methyl (Scheme 1 ), can be prepared via diazomethane reaction. Alternatively compound (2) may be prepared by reacting the unprotected form of (1) with an appropriate alcohol ROH, for example methanol, under acidic conditions. The resulting amino acid ester hydrochloride is N-protected under standard conditions to provide (2) directly. Compound (2)is reacted under mild acid conditions (e.g., p-toluenesulfonic acid) with an appropriate aldehyde, ketone, or acetal/ketal equivalent thereof ((A(CO)B) (e.g., dimethoxypropane, benzaldehyde, cyclohexanone, etc.) to provide ester (3). Ester (3) is converted to the aldehyde (4) either by direct reduction with DIBAL or via the fully reduced alcohol form (e.g., further reaction with DIBAL, LAH, etc.) followed by oxidation (Swern conditions, pyridine sulfur trioxide complex, etc.). The aldehyde (4) can serve as a precursor to the secondary alcohol (5) via reaction with an appropriate nucleophile (e.g., alkyl magnesium halides, alkenylmagnesium halides, alkynyllithium reagents, alkyllithium reagents, etc.). The alcohol (5) may be oxidized to the ketone (6) (e.g., Swern oxidation, pyridine sulfur trioxide complex, pyridinium chlorochromate, etc.). Either the aldehyde (4) or the ketone (6) can then be converted to enolate (7) via the appropriate Wittig, Horner Emmons reagent or their synthetic equivalents (e.g., alkyl (triphenylphosphoranylidene)-acetate, etc.). In the case where (7) arises from compound (4), R"=H. The enolate (7) can be reduced to the allylic alcohol (8) or to the intermediate reduction product aldehyde (9). Aldehyde (9) can also be obtained more directly via the oxidation of alcohol (8) under a number of conditions (see above). The aldehyde (9) can be converted to the alcohol (8) via reaction with reducing agents. The alcohol (8) is reacted with mesylchloride under basic conditions (triethylamine, etc.) to provide the mesylate (10). The mesylate (10)is reacted with sodium azide to provide the azide (11 ). Azide (11) can be reduced under a number of conditions (for example, with triphenylphosphine followed by acid hydrolysis) to provide the amine (12). The amine (12) is guanylated with a variety of guanylation reagents (e.g., N-nitro-S-methylthiopseudouronium salts, etc.) to provide the desired compound (13). Alternatively, the amine nitrogen can be protected with the N-protecting group (P') to provide the intermediate (14).

Compound (14) is reacted with acid under hydrolytic conditions to remove the aldehydic/ketonic group (A(CO)B) (Scheme 1, continued) and provide the compound (15). In some cases the N-protecting group (P) is labile and a second step of N-protection with (P) is required to provide (15). The alcohol (15) can be oxidized to the compound (16) when either $R^3$ or $R^4$ is hydrogen. The protecting group (P') of compound (16) is removed in a standard fashion to provide compound (17). The amine (17) can be guanylated using various guanylation reagents to the provide the compound (18). The protecting group (P) of compound (18) is removed to provide the desired compound (19). In addition, compounds of the type (13) can be reacted under acidic hydrolytic conditions when (P)is an acid labile N-protecting group to provide the desired amino alcohol (20).

An alternative sequence which also provides the desired guanidino compounds is illustrated in Scheme 2. Compounds such as (12) can be reacted with cyanogen bromide under mild basic conditions (triethylamine, etc.) to provide the cyanamide (21). An alternative sequence is the formation of the parent urea via reaction of (12) with trimethylsilylisocyanate or its equivalents (e.g., trichloroacetylisocyanate followed by basic removal of the trichloroacetyl group, etc.) and dehydration (for example, tosyl chloride in pyridine) of the parent urea to the cyanamide (21). The cyanamide (21) is reacted with nucleophiles such as $H_2NR^7$ to provide the guanidino compound (22). This sequence is particularly useful in the cases where ($H_2NR^7$ is hydrazine, substituted hydrazine, hydroxylamine, alkoxyamine, or the like). Compound (22) can be transformed to compound (23). In a manner similar to the transformation of (12) to compound (21), compounds such as (17) can be reacted with cyanogen bromide (or, alternatively, via the sequence involving the intermediate urea form) to produce the cyanamide (24). Compound (24) is converted to the guanidino compound (25) which in turn can be deprotected (loss of (P)) to produce the guanidino compound (26).

Another approach to guanidino compounds is represented in Scheme 3. Compound (12)is reacted with diarylcyanocarbonimidate to provide compound (27) wherein the φ symbol represents the aryl group. Compound (27) can be reacted with a nucleophile Y' to provide compound (28) wherein $R^7$ may represent cyano. Likewise compound (17) can be reacted with diarylcyanocarbonimidate to yield (29), and compound (29) can be reacted with the nucleophile Y' to produce compound (30).

Scheme 4 illustrates the general synthetic paths that may be used to achieve guanylation of compounds; some of these methods have been illustrated in the previous schemes. An amine of general formula (31) (examples from previous schemes include, but are not limited to, compounds (12) and (17))is reacted directly with S-methyl alkylthiopseudouronium salts, N-substituted aminoiminomethanesulfonic acids or the like (for example, S-methyl N-methylthiouronium sulfate, S-methyl N-nitrothiouronium sulfate, or N-ethyl aminoiminomethanesulfonic acid) to provide the product (32) directly. Guanylating reagents such as thiopseudouronium salts, aminoiminosulfonic acids, etc. can generally be prepared from literature sources via the corresponding intermediate urea or thiourea. Compound (31) can also be reacted with isocyanates or isothiocyanates to provide the compound (33). An alternative approach to compound (33) is to first react the amine (31) with phosgene, thiophosgene, or their synthetic equivalents followed by reaction with the amine $H_2NR^7$ providing compound (33)in two sequential steps. In either of these cases, the parent urea or thiourea produced may be alkylated to provide an intermediate isourea or isothiourea form, which when reacted with the nucleophile $NH_2R^7$, provides the compound (32). In this alkylative sequence to produce the desired (32), a thiourea form is preferred owing to the ease of alkylation. In some cases, for compound (33), $R^7$ may represent protecting groups (for example, Cbz, benzoyl, etc.) which can be removed subsequent to the reaction with $NH_2R^7$ to provide the product (32).

Compound (31) is reacted with cyanogen bromide to provide the cyanamide (34). Cyanamide (34) can also be produced via dehydration of the urea form of (33) in the particular case when $R^7$ (in structure (33))is hydrogen. The cyanamide (34) is reacted with the nucleophile $H_2NR^7$ to provide the desired (32).

Another specific synthetic transformation outlined in Scheme 5 is the conversion of nitroguanidino compounds to their corresponding aminoguanidino and guanidino derivatives. For example compounds containing the substructure nitroguanidine represented by (35) are reduced in the presence of zinc and acetic acid to provide the aminoguanidine compounds represented by substructure (36).

As described in Scheme 6, compounds of the amino alcohol type represented by (15), (20), (23), and (32) [wherein $R^4$ is hydroxy] may additionally be reacted with various N-protecting groups (P) to provide additional compounds envisioned by the invention. It is also envisioned that amino alcohols and their N-protected amino alcohol analogs represented, for instance by structures (15), (20), (23), and (32) may also be converted to other N-substituted derivatives by simple alkylative or acylative chemistry performed on the derivatives themselves or various N- and O-protected versions of these compounds. It is also envisioned that amino alcohols and their N-protected amino alcohol analogs represented for instance by structures (15), (20), (23), and

(32) may also be converted to their cyclic acetal forms via the action of an appropriate acetal, ketal, or their synthetic equivalents (A(CO)B equivalent to $R^9(CO)R^{10}$) under acidic conditions to provide compounds of the invention (14), (19), (22), and (37).

As described in Scheme 7, compounds of the amino alcohol type represented by N-protected forms of (15), (20), (23), and (32) [wherein $R^4$ is hydroxy] labeled (15), (20-NP), (23-NP), and (32-NP) may additionally be reacted with electrophiles such as alkyl halides to provide ethers at position $R^4$, compounds (38), (39), (40), and (41) also envisioned in this invention. Final products are prepared by removal of N-protecting groups and/or additional chemistry to install the guanidino group as in the case of compound (38).

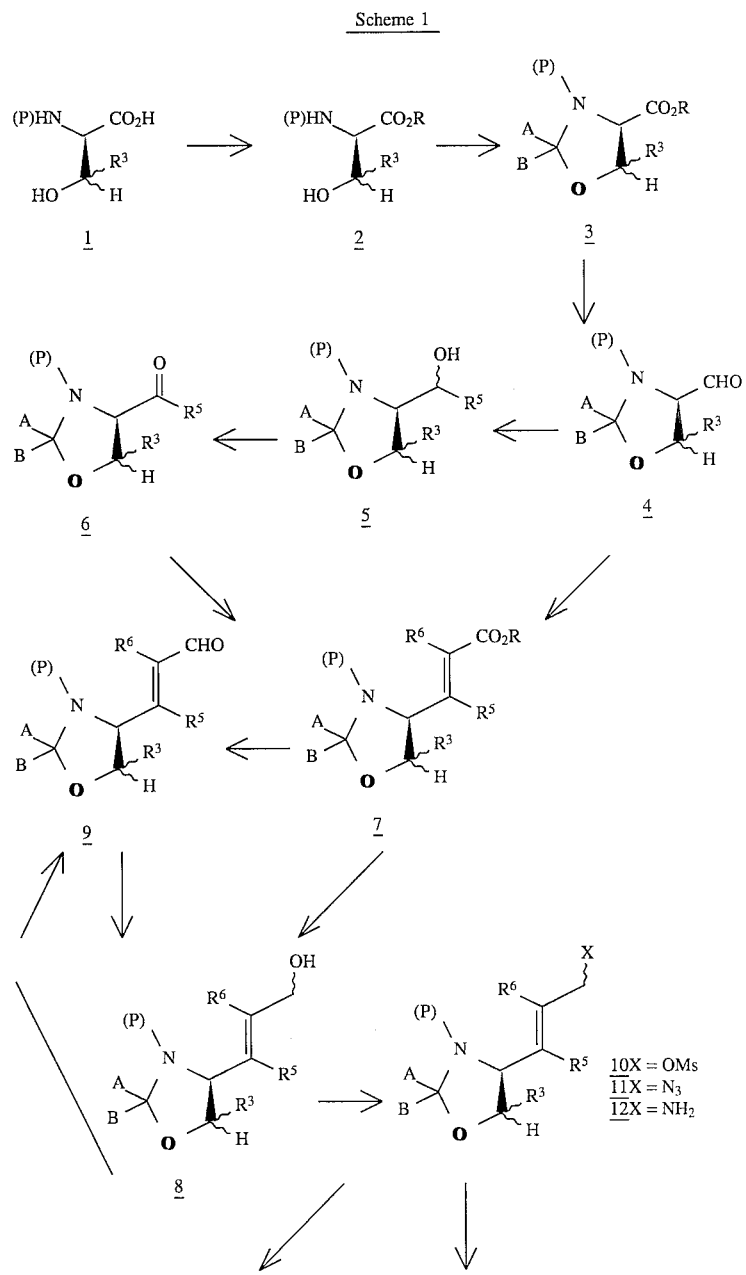

Scheme 1

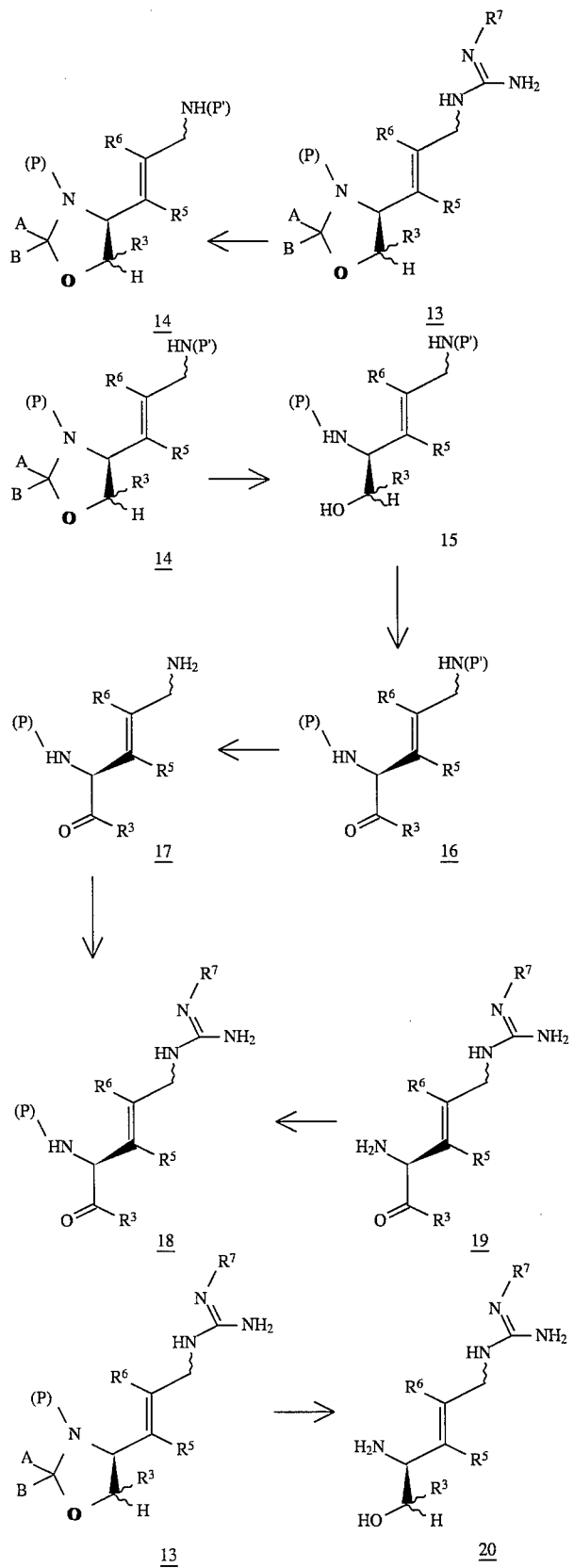

Scheme 2
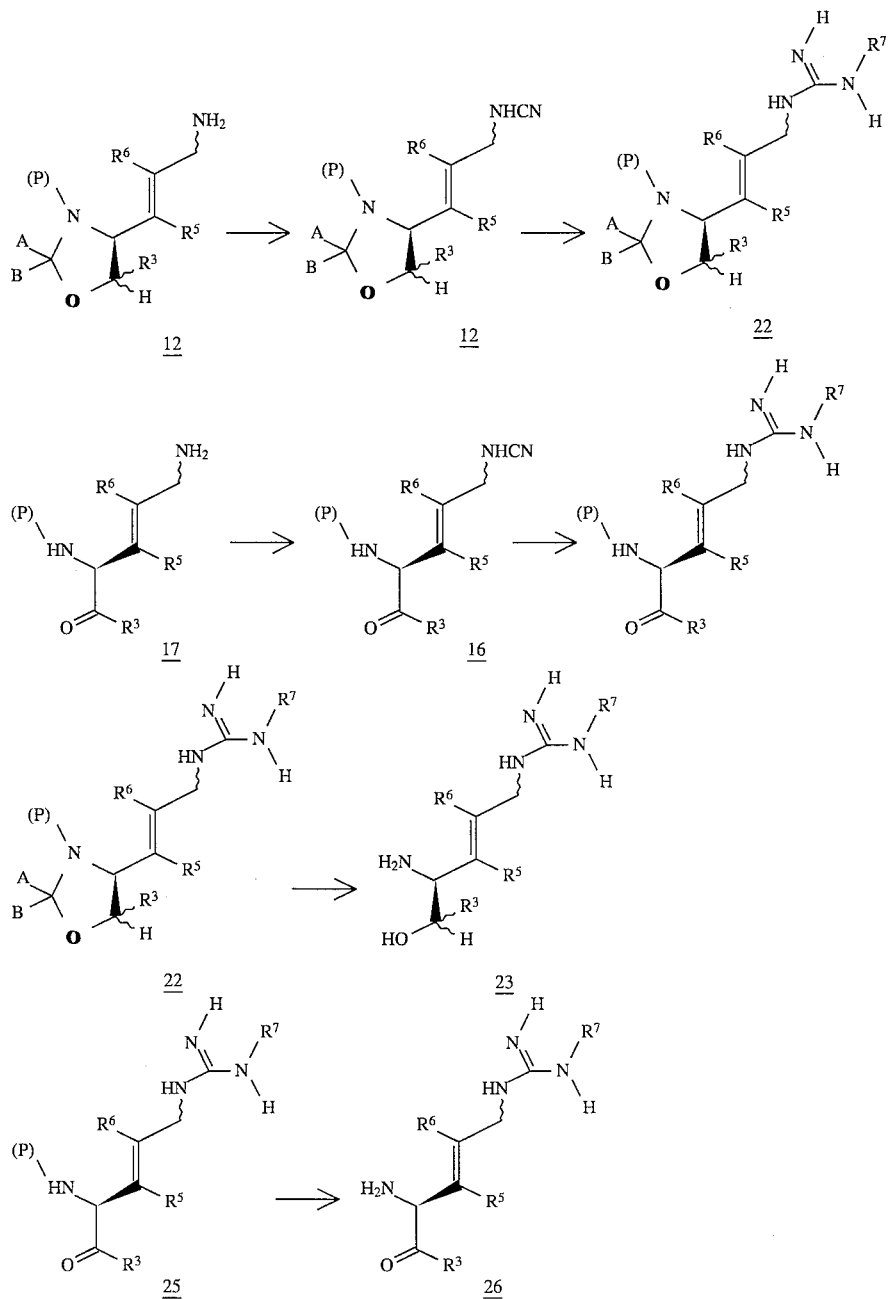

Scheme 3
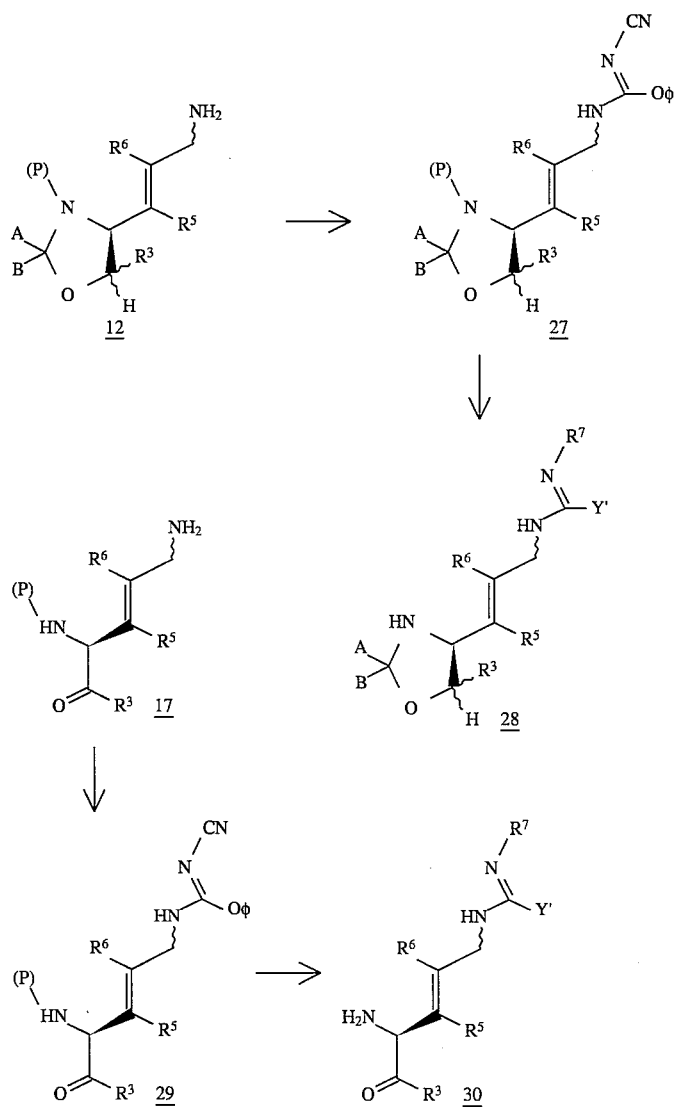

Scheme 4
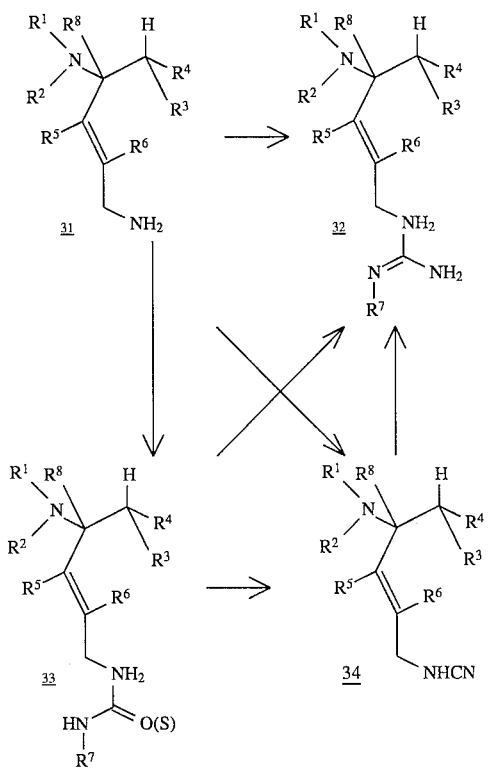
Scheme 5
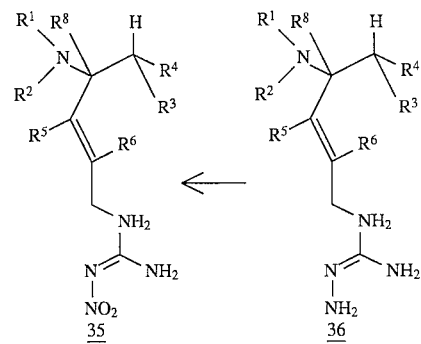
Scheme 6
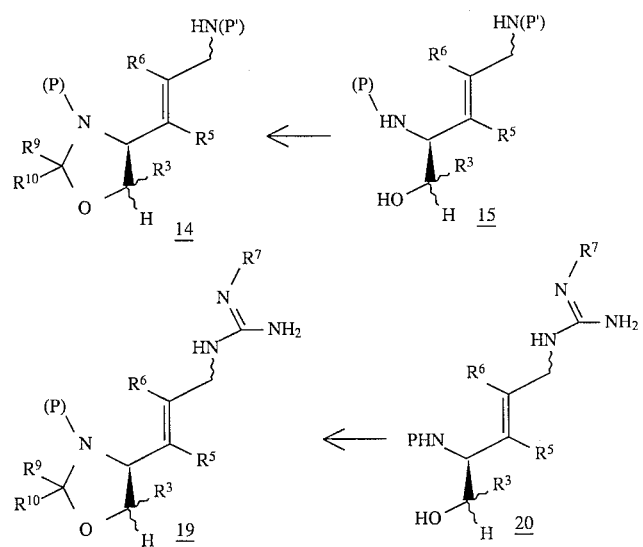

-continued
Scheme 6
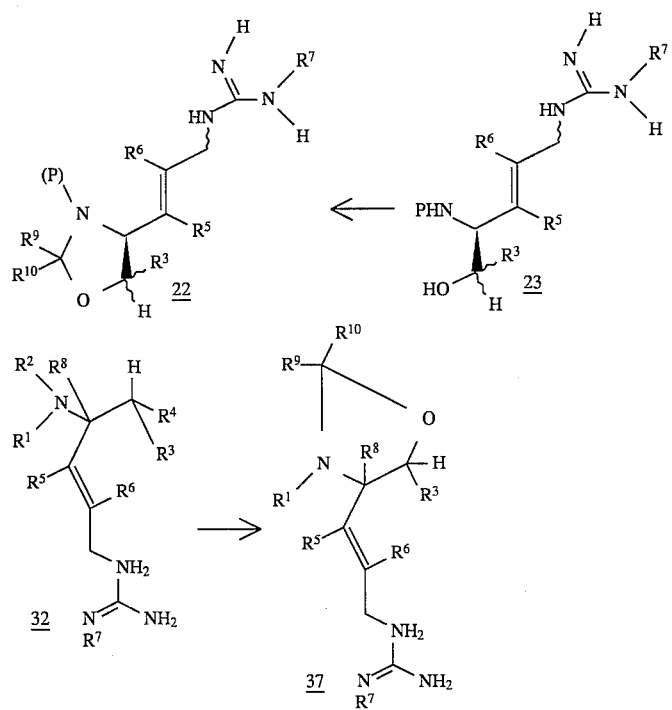
Scheme 7
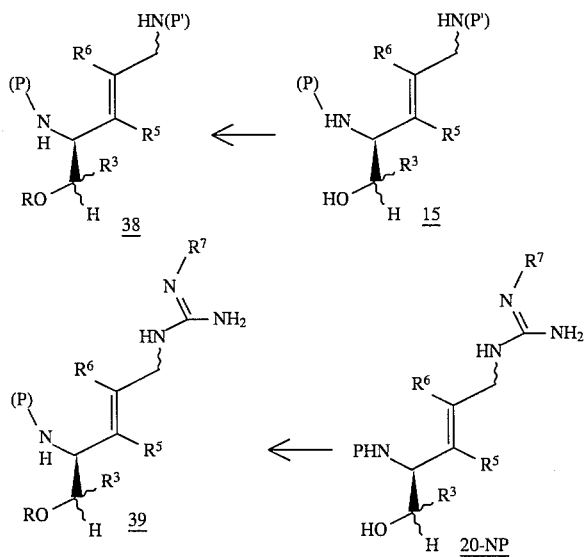

-continued
Scheme 7

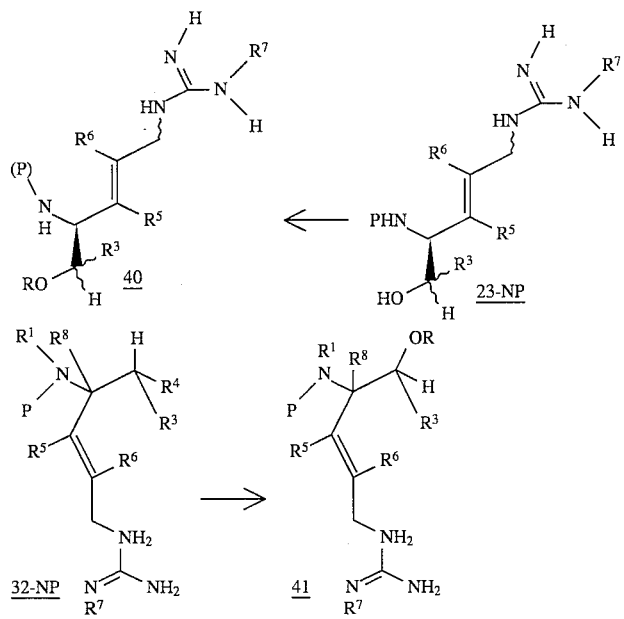

General Experimental Procedures for Bioassays

The enzyme NO synthase produces EDRF/NO and citrulline from L-arginine (Bredt and Snyder, *Proc. Nat'l. Acad. Sci. USA*, 1989, 87: 682–5). The enzymatic generation of EDRF/NO is monitored by measuring the conversion of [$^3$H]-L-arginine to [$^3$H]-L-citrulline. An inhibitor of this specific enzymatic reaction lowers the conversion rate and, thus, the amount of [$^3$H]-L-citrulline produced. Likewise, a compound acting as a substrate would compete with L-arginine and thereby lower the conversion rate.

In those instances where it is suspected that the test substance is acting as a substrate rather than an inhibitor, the EDRF/NO may be estimated. For this confirmation bioassay, a method for quantification of endothelium-derived relaxing factor (EDRF) is utilized and is described in detail below. This technique, measuring cyclic GMP responses of RFL-6 rat fetal lung fibroblast cells to estimate NO or EDRF is sensitive, simple and quite useful for the evaluation of compounds that regulate EDRF/NO release from various endothelial cells, or other cells or tissues (such as for example RAW cells (induced with LPS) and N1E-115 cells). (cf. Ishii, K., et al., *American Journal of Physiology*, 1991, 261:(2 pt 2) H598–603). The cyclic GMP measured is an indirect measure of the amount of EDRF/NO produced by NO synthase, so compounds that reduce the amount of cyclic GMP produced are termed inhibitors of NO synthase, and those that increase cyclic GMP in the absence of exogenous L-arginine are termed substrates or stimulators of NO synthase.

Biological Activity of Exemplified Compounds

[$^3$H]-Arginine to [$^3$H]-Citrulline Conversion

The conversion of L-arginine to L-citrulline was assayed as reported previously (Bredt and Snyder, *Proc. Nat'l Acad Sci USA*, 1989, 87: 682–5) with minor modifications. Briefly, samples of partially purified NO synthase, 50–100 µg of protein or 20 µL of cytosol (alternatively cytosolic preparations from RAW 264.7 cells, a murine monocyte-macrophage cell line, induced for 16 hours with 10 µg/mL medium of Lipopolysaccharide (LPS), or partially purified (phosphocellulose column) type I isozyme from rat brain cerebellum, or partially purified isozyme III from bovine aortic endothelial cells (BAE cells)) were incubated for 20 minutes (3 minutes in the cases of purified enzyme preparations) at 25° C. in the presence of 10 µM L-[2,3-$^3$H] arginine (55 C$_i$/mmol) (containing 34 nM (0.2 µC$_i$)), 1 mM NADPH, and 2 Mm CaCl$_2$ in a final volume of 100 µL. The reaction was stopped by adding 1 mL of stop buffer (2 mM EGTA, 2 mM EDTA 20 mM Hepes, pH 5.5). The total volume was then applied to a 1 mL Dowex AG 50 WX-8 column (Na$^+$ form, Bio-Rad) that had been pre-equilibrated with the stop buffer. L-[2,3-$^3$H]Citrulline was eluted (2×) with 0.5 mL of stop buffer and radioactivity was determined by liquid scintillation counting.

cGMP Assay-(Rat Fetal Lung Fibroblast (RFL-6) cells as detectors of EDRF/NO)

This is a new bioassay method for detection and quantification of endothelium-derived relaxing factor (EDRF) wherein cyclic GMP responses of RFL-6 rat fetal lung fibroblast cells are utilized to estimate the activity of nitric oxide (NO) and EDRF. The conditioned medium from bovine aortic endothelial (BAE) cells cultured in tissue culture plates (alternatively cytosolic preparations from a murine macrophage cell line (RAW cells) induced for 16 hr with 10 µg/mL medium of LPS, partially purified (phosphocellulose column) type I isozyme from rat brain cerebellum, partially purified isozyme III from BAE cells, or RAW cells cultured in tissue plates and induced for 16 hr with 10 µg/mL LPS, or N1E-115 neuroblastoma cells cultured in tissue plates) was quickly transferred to RFL-6 incubations in order to determine EDRF/NO. In the presence of superoxide dismutase, RFL-6 cells cultured in 6-well tissue culture plates exhibited very high sensitivities to both NO and EDRF: e.g., they responded to NO at a concentration as low as 2 nM and the basal release of EDRF from 1–2×10$^6$ BAE cells. Based on the lower detection limit of the radioimmunoassay for cyclic GMP, calculations reveal that 100–200 fmoles of NO and the basal EDRF release from 1–2×10⁵ BAE cells can be detected with RFL-6 cells by choosing smaller culture wells. Thus, this method is more sensitive than any other currently available. This bioassay technique for EDRF/NO is sensitive, simple and quite useful for the evaluation of experimental conditions and compounds that regulate EDRF/NO release from various endothelial cells and other cells and tissues, for instance RAW cells (induced with LPS), N1E-115 cells, their homogenates in various states of purity and any other EDRF/NO generating system.

RFL-6 Cell Culture Method

Rat fetal lung fibroblast cells (RFL-6, Stanford University, California) were grown in 6-, 12-, 24- or 48-well tissue culture plates containing F-12 Ham's nutrient mixture supplemented with 15% uninactivated fetal bovine serum. Bovine aortic endothelial (BAE) cells (NIGMS, Human Genetic Mutant Cell Repository, Camden, N.J.) were cultured in the 6-well plates containing Eagle's Minimum Essential Medium (MEM) supplemented with 20% fetal bovine serum and MEM nonessential amino acids (0.1 mM each). Both culture media contained 2 mM L-glutamate, 100 U/mL penicillin and 0.1 mg/mL streptomycin. Cells were maintained at 37° C. under an atmosphere of 95% air: 5% $CO_2$.

Detection Of EDRF/NO with RFL-6 Cells

BAE cells (RAW cells [induced with LPS], N1E-115 cells, rat brain homogenate passed through a phosphocellulose column, etc.) grown to confluence in 6-well plates were used as the source of EDRF/NO. After removing the culture medium, cells were washed twice with 2 mL of Lockes solution (without IBMX) and equilibrated for 20 minutes in 1 mL of Lockes buffer containing 20 U/mL of SOD in the presence or absence of 100 μM L-arginine, $N^G$-nitro-L-arginine (NNA), or the test compounds for 15 min before stimulation with 3 μM ADP for 3 minutes (no stimulation is necessary for homogenate sources of enzyme or those cells induced with LPS, neurotensin is used to stimulate N1 E-115 cells). Following exposure of BAE cells to ADP for 3 minutes, an aliquot of the conditioned medium was transferred to the RFL-6 incubations with a Pipetman® micropipette. Volumes of the conditioned medium transferred were 1000 μL, 400 μL, 200 μL and 100 μL when RFL-6 cells were incubated in the 6-, 12-, 24- and 48-well plates, respectively.

Before transferring the conditioned medium from BAE cells, RFL-6 cells cultured to confluence were washed twice with a Ca and Mg free PBS then equilibrated in Locke's buffer (with 0.3 mM IBMX, 20U/mL of SOD). The volume for preincubation was 500 μL –1000 μL. After incubating RFL-6 cells with conditioned medium from BAE cells (or other EDRF/NO producing systems) for the indicated time periods (~3 minutes), the medium was removed and ice-cold 50 mM sodium acetate buffer (pH 4.0) was added to each well to stop the reaction followed by liquid nitrogen. Cyclic GMP levels in RFL-6 cells were determined by RIA (radioimmunoassay) or samples could be stored at −70° C. until radioimmunoassay.

For assaying pure enzyme or homogenates containing active enzyme, the following alterations are made in the procedure: after preparation of the RFL cells by preincubation, a fresh Lockes buffer is added containing SOD and IBMX as before. In addition L-arginine (100 μM), NADPH (100 μM), $BH_4$ (3 μM), calmodulin (100 μ/mL when necessary) and the test compound(s) are added followed by the enzyme homogenate to a final adjusted volume of 1–2 mL. Incubations proceed at 37° C. for 3 minutes followed by the same termination steps as above. cGMP is again measured by RIA.

The following Tables present data on the inhibition of [³H]-citrulline formation from [³H]-L-arginine by the compounds of the invention in various preparations representative of the isoforms of NOS, Types I, II, and III NOS as represented by rat brain cytosol, RAW 247.7 macrophage cell cytosol, and BAE homogenate preparation respectively.

TABLE I

Percent Inhibition of [³H]-Citrulline Formation at 100 μM

| Example No. | Rat Brain Cytosol | RAW Cell Cytosol | BAE Preparation |
|---|---|---|---|
| 1 | 6 | 0 | nd |
| 2 | 80 | 14 | nd |
| 3 | 35 | 68 | nd |
| 4 | nd | 50 | 22 |
| 6 | 0** | 46* | 0** |
| 7 | nd | 17 | nd |
| 8 | 23 | 13 | nd |
| 9 | 51 | 47 | nd |
| 10 | 74 | 43 | 40 |
| 11 | 20 | 41 | nd |
| 12 | 70 | 8 | 5 |
| 14 | 0 | 0 | nd |
| 15 | 90 | 66 | 50 |
| 17 | 18 | 6 | nd |
| 18 | 17 | 9 | nd |
| 19 | 77 | 27 | 0 |
| 20 | 27 | 45 | nd |
| 21 | 86 | 94 | 50 |
| 22 | 70 | 97 | 50 |
| 24 | 35 | 20 | nd |
| 25 | 80 | 20 | 14 |
| 27 | 86 | 97 | 46 |

* tested at 10 μM
** tested at 30 μM

TABLE II

Inhibition of [³H]-Citrulline Formation $IC_{50}$ (μM)

| Example No. | Rat Brain Cytosol | RAW Cell cytosol | BAE Preparation |
|---|---|---|---|
| 1 | >100 | >100 | >100 |
| 2 | 40 | >100 | 80 |
| 3 | >100 | 40 | >100 |
| 4 | nd | 100 | >100 |
| 6 | >30 | 22 | >30 |
| 7 | nd | >100 | nd |
| 8 | >100 | >100 | nd |
| 9 | 80 | 100 | nd |
| 10 | 30 | >100 | >100 |
| 11 | >100 | >100 | nd |
| 12 | 30 | >100 | >100 |
| 14 | >100 | >100 | >100 |
| 15 | 10 | 40 | 100 |
| 17 | >100 | >100 | nd |
| 18 | >100 | >100 | nd |
| 19 | 35 | >100 | >100 |
| 20 | >100 | 100 | nd |
| 21 | 20 | 30 | 100 |
| 22 | 40 | <100 | 100 |
| 24 | >100 | >100 | nd |
| 25 | 40 | >100 | >100 |
| 27 | 20 | 20 | >100 |

The following examples, which are provided for illustration and not limitation of the invention, will serve to further illustrate preparation of the novel compounds of the invention and biological activity thereof.

EXAMPLE 1

3-(1,1-Dimethylethyl)-(S)-4-(3-N$^G$-nitroguanidinopropen-1, E-yl)-2,2-dimethyl-3-oxazolidinecarboxylate Step 1a, N-[(1,1-Dimethylethoxy)carbonyl]-D-serine methyl ester To a solution of D-Boc-serine (25 mmol) in EtOH cooled to 0° C. was added diazomethane (4–5 eq) in a solution of Et$_2$O. After the addition of the diazomethane, the reaction was stirred for one hr and then quenched with glacial HOAc. The product was extracted with EtOAc. The combined organic extracts were washed with NaHCO$_3$ and brine, dried over MgSO$_4$, and concentrated in vacuo. Purification by flash chromatography eluting with hexane/EtOAc (1:1) afforded the product (72%) as a yellow liquid: R$_F$ 0.75 (EtOAc:hexane 1:1); $^1$H NMR (300 MHz, CDCl$_3$)δ1.47 (s, 9H), 2.48 (s, 1H), 3.82 (s, 3H), 3.90 (dd, J=4, 12 Hz, 1H), 3.95 (dd, J=4,12 Hz, 1H), 4.40 (m, H), 5.45 (m, H); $^{13}$C NMR (75 MHz, CDCl$_3$) δ: 21.2, 52.5, 55.6, 60.4, 63.1, 80.2, 155.7, 171.4; MS(DCI) m/e 220 (m+H)$^+$, 237 (m+NH$_4$)$^+$. Analysis calc'd for C$_9$H$_{17}$NO$_5$0.5 H$_2$O: C, 47.36; H, 7.95; N, 6.14. Found: C, 47.20; H, 7.58; N, 6.12.

Step 1b, 3-(1,1 -Dimethylethyl)4-methyl-(R)-2,2-dimethyl-3,4 -oxazolidinecarboxylate To a solution of the methyl ester of Example 1a (4.8 mmol) in benzene was added 2-methoxypropane (2 eq) and p-toluene sulfonic acid (0.1 eq), and the reaction was heated to reflux for 48 hr. The reaction mixture was extracted with EtOAc and the combined organic extracts were washed with brine and H$_2$O, dried over MgSO$_4$, and concentrated in vacuo. Purification by flash chromatography eluting with EtOAc and hexane afforded the product as a yellow liquid in 78% yield: R$_F$ 0.5 (1:1 hexane:EtOAc); $^1$H NMR (300 MHz, CDCl$_3$) δ: 1.50 (s, 9H), 1.55 (br s, 3H), 1.64 (s, 3H), 3.80 (s, 3H), 4.25 (m, 1H), 4.38 (dd=5, dd, J=9 Hz, 1H), 4.50 (dd, J=6, 8.5 Hz, 1H); MS(DCI) m/e 260 (m+H)$^+$, 277 (m+NH$_4$)$^+$, 221 (m-C$_4$H$_9$). Analysis calc'd for C$_{12}$H$_{21}$NO$_5$.0.75 CH$_2$Cl$_2$: C, 46.56; H, 6.90; N, 4.22. Found: C, 46.86; H, 6.67; N, 4.29.

Step 1c. 1,1-Dimethylethyl (R)-4-formyl-2, 2-dimethyl-3-oxazolidinecarboxylate

To a solution of the methyl ester of Example 1b (17.8 mmol) in toluene cooled to −78° C. was added 1M DIBAL (2.2 eq) over a 15–20 minute period. The reaction was stirred for 3–4 hr at −78° C. and then quenched with MeOH at −78° C. The reaction was extracted with EtOAc and the combined organic extracts were washed with NaOH, H$_2$O and brine, dried over MgSO$_4$, and concentrated in vacuo to afford the product as a colorless oily solid (64%): R$_F$ 0.45 (1:1 EtOAc:hexane); $^1$H NMR(300 MHz, CDCl$_3$) δ: 1.49 (s, 9H), 1.52 (s, 3H), 1.58 (s, 3H), 3.80 (m, 1H), 4.20 (m, 2H), 4.40 (m, 1H), 9.53 (br s, 1H); MS(DCl) m/e 2.30 (m+H)$^+$, 247 (m+NH$_4$)$^+$, 191 (m-C$_4$H$_9$); [α]$_D^{20}$=−24.72° (c=1.0, EtOH).

Step 1d. 3-(1,1-Dimethylethyl)-(S)-4-(3-(ethoxypropen-2E-oyl))-2,2-dimethyl-3-oxazolidinecarboxylate To a solution of the aldehyde of Example 1c (40.5 mmol) (which was freshly prepared) in THF at ambient temperature was added ethyl (triphenylphosphomnylidene)acetate (1.5 eq). The reaction was stirred at ambient temperature for 4–6 hr and then concentrated in vacuo. Purification by flash chromatography eluting with hexane-EtOAc afforded the title compound as a colorless crystalline solid (83%): R$_F$ 0.6 (1:1 EtOAc:hexane); $^1$H NMR(300 MHz, CDCl$_3$) δ: 1.29 (t, 3H), 1.42 (s, 9H), 1.51 (br s, 3H), 1.54 (br s, 3H), 1.63 (d, 2H), 3.82 (dd, J=3.0, 9.6 Hz, 1H), 4.20 (dd, J=7.5, 12.6 Hz, 1H), 4.40 (m, 1H), 5.83 (t, 1H), 9.80 (m, 1H); $^{13}$C NMR (75 MHz, CDCl$_3$) δ: 166.1, 122.3, 94.4, 80.2, 67.2, 60.4, 28.3, 27.2, 26.4, 24.6, 23.5, 14.2; MS(DCI) m/e 300 (m+H)$^+$, 317 (m+H)$^+$, 3.17 (m+NH$_4$)$^+$, 261 (m-C$_4$Hg), 200 (m+H-Boc). Analysis calc'd for C$_{15}$H$_{25}$NO$_5$.0.10 EtOAc.0.20 H$_2$O : C, 59.32; H, 8.47; N, 4.49. Found: C, 59.27; H, 8.52; N, 4.73.

Step 1e. 3-(1,1-Dimethylethyl)-(S)-4-(3-hydroxypropen-1, E-yl)-2,2-dimethyl-3-oxazolidinecarboxylate To a solution of the ethyl ester from Example 1 d (61.8 mmol) in anhydrous toluene cooled to −78° C. was added DIBAL (5 eq) over a 30 minute period. The reaction was stirred at −78° C. for 3 hr while following by tlc and then quenched at −78° C. with MeOH. The product was extracted with EtOAc and the combined organic extracts washed with NaOH, H$_2$O, and brine, dried over MgSO$_4$, and concentrated in vacuo. Purification by flash chromatography with hexane/EtOAc (1:1) afforded the product as a colorless oil (98%): R$_F$ 0.30 (1:1 EtOAc:hexane); $^1$H NMR(300 MHz, CDCl$_3$) δ: 1.50 (s, 9H), 1.53 (s, 3H), 1.61 (s, 3H), 3.75 (dd, J=4.5, 9.0 Hz, 1H), 4.05 (dd, J=9.0, 16.0 Hz, 1H), 4.20 (d, 2H), 5.70 (m, 2H); MS(DCI) m/e 258 (m+H)$^+$, 275 (m+NH$_4$)$^+$, 219 (m-C$_4$H$_9$); Analysis calc'd for C$_{13}$H$_{23}$NO$_4$10.25 CH$_2$Cl$_2$: C, 60.68; H, 9.01; N, 5.44. Found: C, 60.31; H, 8.64; N, 5.19.

Step 1f. 3-(1,1-Dimethylethyl)-(S)-4-(3-mesyloxypropen-1, E-yl)-2,2-dimethethyl-3-oxazoildinecarboxylate To a solution of the alcohol from Example 1e (12.0 mmol) in CH$_2$Cl$_2$ at 0° C. was added TEA (2 eq) and mesyl chloride (1.5 eq). The reaction was stirred at 0° C. for 30 minutes and then extracted with CH$_2$Cl$_2$. The combined organic extracts were washed with cold H$_2$O, cold 10% HCl, NaHCO$_3$ and brine, dried over MgSO$_4$ and concentrated in vacuo. Purification by flash chromatography eluting with hexane/EtOAc (1:1) afforded the title compound as a colorless liquid (84%): RF 0.65 (1:1 EtOAc:hexane); $^1$H NMR(300 MHz, CDCl$_3$) δ: 5.70 (m, 1H), 4.23 (d, J=6.0 Hz, 2H), 4.18 (dd, J=9.5, 12 Hz, 1H), 3.75 (dd, J=3.5, 9 Hz, 1H), 3.10 (s, 2H), 1.60 (m, 3H), 1.57 (s, 3H), 1.52 (s, 3H), 1.48 (s, 9H); MS(DCI) m/e 336 (m+H)$^+$, 353 (m+NH$_4$)$^+$, 297 (m-C$_4$H$_9$+NH$_4$)$^+$; Analysis calc'd for C$_{14}$H$_{25}$NO$_6$S: C, 50.13; H, 7.51; N, 4.18. Found: C, 49.69H, 6.29; N, 4.73.

Step 1g. 3-(1,1-Dimethylethyl)-(S)-4-(3-azidopropen-1,E-yl)-2,2-dimethyl-3-oxazolidinecarboxylate To a solution of the mesylate from Example 1 f (19 mmol) at ambient temperature in MeOH/H$_2$O (10:1) was added sodium azide (1.2 eq). The reaction was stirred for 2 hr and extracted with EtOAc. The combined organic extracts were washed with H$_2$O and brine, dried over MgSO$_4$, and concentrated in vacuo. Purification by flash chromatography eluting with hexane/EtOAc (1:1) afforded the title product as a colorless oil (76%): R$_F$ 0.65 (1:1 hexane:EtOAc); $^1$H NMR(300 MHz, CDCl$_3$) δ: 5.75 (m, 1H), 5.37 (d, J=16.5 Hz, 1H), 4.08 (dd, J=6.0, 14.0 Hz, 1H), 3.90 (m, 1H), 3.28 (d, J=6.0 Hz, 2H), 3.23 (d, J=3.0 Hz, 2H), 1.60 (s, 3H), 1.55 (s, 3H), 1.45 (s, 9H); $^{13}$C NMR (75 MHz, CDCl$_3$) δ: 124.8, 68.1, 58.4, 52.0, 28.4, 27.4, 26.6, 24.4, 24.7, 23.6, 23.5; MS(DCI) m/e 283 (m+H$^+$), 300 (m+NH$_4$$^+$), 244; Analysis calc'd for C$_{13}$H$_{22}$N$_4$O$_3$.0.15 CH$_2$Cl$_2$: C, 53.53; H, 7.62; N, 18.99. Found: C, 53.64; H, 7.80; N, 18.66.

Step 1h. 3-(1,1-Dimethylethyl)-(S)-4-(3-aminopropen-1,E-yl)-2,2-dimethyl-3 -oxazolidinecarboxylate To a solution of the azide from Example 1g (14.2 mmol) in isopropanol at ambient temperature was added sodium borohydride (3 eq). The reaction was heated at reflux for 24 hr, followed by tlc and extracted with EtOAc. The combined organic extracts were washed with H$_2$O and brine, dried over MgSO$_4$ and concentrated in vacuo. Purification by flash chromatography eluting with EtOH/H$_2$O (2:1) containing 3% NH$_4$OH afforded the title compound as a colorless liquid (67%): R$_F$ 0.30 (2:1 EtOH:H$_2$O containing 3% NH$_3$); $^1$H NMR(300 MHz, CDCl$_3$) δ: 5.70 (m, 2H), 4.37 (bd, 2H), 4.05 (dd, J=5.0, 9.0 Hz, 1H), 3.80 (d, J=10 Hz, 1H), 4.42 (m, 1H), 1.58 (s, 3H), 1.56 (s, 3H), 1.45 (s, 9H); $^{13}$C NMR(75 MHz, CDCl$_3$) δ: 128.2, 93.7, 79.4, 68.2, 58.7, 43.4, 28.4, 27.7, 26.5, 24.7, 23.6; MS(DCl) m/e 201 (m-C$_4$H$_9$) $^+$, 257 (m+H)$^+$; [α]$_D^{20}$=+49.29° (c=0.355, CH$_2$Cl$_2$); Analysis calc'd for C$_{13}$H$_{24}$N$_2$O$_3$: C, 60.91; H, 9.44; N, 10.93. Found: C, 57.23; H, 9.43; N, 10.31.

Step 1i. 3-(1,1-Dimethylethyl)-(S)-4-(3-N$^G$-nitroguanidino-propen-1,E-yl)2,2-dimethyl-3-oxazolidinecarboxylate To a solution of the amine from Example 1h (0.040 g) in EtOH/H$_2$O (1:1) was added the N-nitro-S-methylpseudothioure (1 eq) and TEA (1 eq). The reaction was stirred at ambient temperature for 48 hr and then concentrated in vacuo. Purification by flash chromatography eluting with EtOAc:CH$_2$Cl$_2$ (3:1) afforded the title compound as a white solid (90%): R$_F$ 0.75 EtOAc:CH$_2$Cl$_2$ (3:1); $^1$H NMR(300 MHz, CDCl$_3$) δ: 1.42 (s, 9H), 1.45 (s, 3H), 1.53 (s, 3H), 3.69 (dd, 1H, J=5.1, J=1.2Hz), 3.83 (m, 2H), 4.02 (m, 1H), 4.31 (t, 1H, J=3Hz), 5.65 (m, 2H); $^{13}$C NMR(75 MHz, CDCl$_3$) δ: 23.5, 25.2, 26.95, 28.4, 43.1,58.8, 67.9, 93.9, 127.9, 132.9, 152.3, 160.4; MS(DCl) m/e 344 (m+H)$^+$, 299, 244 (m-Boc+H)$^+$; MS(FAB) m/e 344 (m+H$^+$); [α]$_D^{20}$=+42.71° (c=1.25, H$_2$O); Analysis calc'd for C$_{14}$H$_{25}$N$_5$O$_5$: C, 48.97; H, 7.34; N, 20.40. Found: C, 49.01; H, 7.46; N, 20.20.

EXAMPLE 2

N$^G$-Nitroguanidinyl-4(S)-amino-pent-2,E-ene-5-ol

A solution of the product from Example 1i in 3N HCl in 66% HOAc was stirred at rt for 24 hr. The reaction mixture was concentrated in vacuo. The residue was purified by chromatography over silica gel using CH$_3$CN/HOAc/H$_2$O (6/1/1) as the elutant. The yield was 62%: R$_F$ 0.35 (CH$_3$CN/HOAc/H$_2$O; 6/1/1 ); [α]$_D^{20}$ =+6.18° (c=0.10, MeOH); [α]$_D^{20}$=+23.62° (c=0.10, H$_2$O); $^1$H NMR(300 MHz, D$_2$O) δ: 3.66 (dd, 1H, J=11.7, 6.3 Hz), 3.83 (dd, 1H, J=11.7, 3.6 Hz), 3.97 (m, 3H), 5.70 (dd, 1H, J=15.5, 7.5 Hz), 6.00 (dt, 1H, J=15.5, 4.5 Hz); $^{13}$C NMR(75 MHz, D$_2$O) δ: 44.8, 56.9, 64.3, 126.7, 134.7, 161.8; MS(DCl) m/e 204 (m+H)$^+$; Analysis calc'd for C$_6$H$_{13}$N$_5$O$_3$.6 HCl.0.80 H$_2$O: C, 16.51; H, 4.76; N, 16.05. Found: C, 16.58; H, 4.64; N, 15.91.

EXAMPLE 3

3-(1,1-Dimethylethyl)-(S)-4-(3-guanidinopropen-1,E-yl)-2,2-dimethyl-3-oxazolidinecarboxylate To a solution of the amine from Example 1h (0.081 7 g)in EtOH/H$_2$O (2:1) (10 mL) at ambient temperature was added S-methylpseudothiouronium sulfate (1.33 eq) and TEA (2 eq). The reaction was stirred at rt for 72 hr and then concentrated/n vacuo. Purification of the residue by flash chromatography eluting with EtOAc:CH$_2$Cl$_2$(3:1) afforded the product as a colorless oil (62%): R$_F$ 0.50 (EtOH:H$_2$O, 2:1 ); $^1$H NMR(300 MHz, CD$_3$OD) δ: 1.47 (s, 9H), 1.52 (s, 3H), 1.56 (s, 3H), 3.70 (dd, 1H, J=1.6, 7.8 Hz), 3.80 (d, 2H, J=3.4 Hz), 4.10 (dd, 1H), J=5.3, 11.0 Hz), 4.40 (m, 1H), 5.63 (m, 2H); MS(FAB/MAT90) m/e 299 (m+H$^+$); [α]=+19.42° (c=0.80, EtOH); Analysis calc'd for C$_{14}$H$_{26}$N$_4$O$_3$; C, 49.68; N, 8.46; N, 13.63. Found: C, 49.76; H, 8.32; N, 13.97.

EXAMPLE 4

1-Guanidirlyl-4(S)-amino-pent-2,E-ene-5-ol

A solution of the protected guanidine from Example 3 (0.2 mmol) in 4N HCl was stirred at rt for 24 hr. The reaction was concentrated in vacuo. The residue was purified on silica gel and eluted with CH$_3$CN/HOAc/H$_2$O 4/1/1. The product was a white glass and obtained in 25% yield: R$_F$ 0.34 (CH$_3$CN/HOAc/H$_2$O 4/1/1); [α]$_D^{20}$=+17.48° (c=0.15, H$_2$O); $^1$H NMR(300 MHz, D$_2$O) δ: 3.68 (dd, 1H, J=11.7, 6.6 Hz), 3.84 (dd, 1H, J=11.7, 4.5 Hz), 3.92 (d, 2H, J=4.5 Hz), 3.95 (m, 1H), 5.73 (dd, 1H, J=15.5, 7.5 Hz), 5.98 (dt, 1H, J=15.5, 4.5 Hz); MS (DCl/NH$_3$) m/e 159 (m+H$^+$); Analysis calc'd for C$_6$H$_{14}$N$_4$O.2.0 HCl.0.7 H$_2$O: C, 29.57; H, 7.20; N, 22.99. Found: C, 29.82; H, 7.06; N, 22.86.

EXAMPLE 5

3-(1,1-Dimethylethyl)-(S)-4-(3-N$^G$-aminoguanidino-propen-1,E-yl)-2,2-dimethyl-3-oxazolidinecarboxylate The material from Example 1h (3-(1,1-dimethylethyl)-(S)-4-(3 -aminopropen-1,E-yl)-2,2-dimethyl-3-oxazolidinecarboxylate) (127 mg, 0.5 mmol) and TEA (153 μL, 1.1 mmol) were dissolved in 5 mL Et$_2$O and treated with cyanogen bromide (CNBr, 183 μL, 0.55 mmol, 3M in CH$_2$Cl$_2$) in 1 portion. After 10 min, 5 mL EtOH and NH$_2$NH$_2$.HCl (35.9 mg, 0.55 mmol) were added. After 1 day, additional NH$_2$NH$_2$.HCl (36 mg) was added and the reaction mixture was heated at 80° C. for 3 days. The cooled reaction mixture was chromatographed on silica gel, eluted with 5:2 EtOAc-PAW to provide diaminotriazole (by-product resulting from over cyanation, MW=338, 24 mg, 0.07 mmol, 14%) followed by desired product 110.6 mg, 0.35 mmol, 71% yield (cf. Wagenaar and Kerwin, J. Org. Chem. 1993, 58: 4331–4338): [α]$_D^{20}$=+40.6° (c=0.17, CDCl$_3$); 1H NMR (300 MHz, CD$_3$OD)δ1.42–1.53 (m, 12H), 1.55–1.58 (m, 3H), 3.52 (d, J=6 Hz, 0.5H), 3.73 (dt, J=2, 12 Hz, 1H), 3.83–3.86 (m, 1.5H), 4.05–4.12 (m, 1H), 4.37 (bs, 1H), 5.58–5.76 (m, 1.5H), 5.86 (ddt, J=15, 7, 1 Hz, 0.5H); MS;(DCl) m/e 314 (m+H)$^+$, 257, 158.

EXAMPLE 6

N$^G$-Aminoguanidinyl-4(S)-amino-pent-2,E-ene-5-ol

The product of Example 5 (91 mg, 0.29 mmol) was treated with 3 mL 6N HCl for 2 hr and then the reaction mixture was diluted and lyophilized. The crude product was chromatographed on silica gel eluted with 1:2 EtOAc-PAW to provide 27.1 mg, 0.11 mmol, 38% yield: R$_F$ 0.2 (1:2 EtOAc-PAW); 2 spots observed by tlc and confirmed by 2d-tlc.; [α]$_D^{20}$=+10.0° (c=0.08, CD$_3$OD); $^1$H NMR (500 MHz, D$_2$O) δ: 3.66–3.73 (m, 2.3H), 3.81–3.85 (m, 1.7H), 3.92–4.03 (m, 3H), 5.68–5.74 (m, 0.7H), 5.92–6.05 (m, 1.3H); MS(DCl)m/e 174(m+H)$^+$, 134, 119, 117.

EXAMPLE 7

3-(1,1-Dimethylethyl)-(S)-4-(3-N$^G$-hydroxyguanidino-propen-1,E-yl)-2.2-dimethyl-3-oxazolidinecarboxylate The material from Example 1h (3-(1,1-dimethylethyl)-(S)-4-(3 -aminopropen-1 ,E-yl)-2,2-dimethyl-3-oxazolidinecarboxylate) (512 mg, 2 mmol) was dissolved in 20 mL of Et$_2$O and treated with CNBr (732 μL, 2.2 mmol, 3M in CH$_2$Cl$_2$), followed by TEA (613 μL, 4.4 mmol). After 10 minutes, EtOH (20 mL) and NH$_2$OH.HCl (306 mg, 4.4 mmol) were added and the reaction was stirred overnight at rt (cf. Wagenaar and Kerwin, *J. Org. Chem.* 1993, 58: 4331–4338). After evaporation of the solvent, chromatography of the residue and elution with 5:1 EtOAc-PAW resulted in 602 mg of product, 1.91 mmol, 96% yield: $R_F$ 0.2 (5:1 EtOAc-PAW); $^1$H NMR (300 MHz, CD$_3$OD) δ: 1.4–1.5 (m, 12H), 1.57 (s, 3H), 3.73 (dd, J=2, 9 Hz, 1H), 3.86 (d, J=4 Hz, 2H), 4.07 (dd, J=7, 9 Hz, 1H), 4.37 (bs, 1H), 5.58–5.78 (m, 2H); $^3$C NMR (75 MHz, CD$_3$OD) δ: 23.6, 23.8, 25.0, 27.0, 27.6, 28.7, 43.0, 60.0, 69.0, 81.2, 81.9, 95.1, 127.3, 132.6, 133.5, 160.3; MS(DCl) m/e 315 (m+H)$^+$; MS(DCl) calc'd for C$_4$H$_{27}$N$_4$O: m/e 315.2032, found: 315.2020; $[\alpha]_D^{23}$=+29.3° (c=1.1, MeOH).

Example 8

N$^G$-Hydroxyguanidinyl-4(S)-amino-pent-2,E-ene-5-ol

The product of Example 7 (19.6 mg, 0.062 mmol) was treated with 5 mL of 4N HCl in dioxane at 4° C. and allowed to reach rt. After 1 hr, the reaction mixture was filtered and the resulting solid was rinsed with Et$_2$O. The hygroscopic solid was dissolved in H$_2$O and lyophilized to provide 11.4 mg, 83% yield: $^1$H NMR (300 MHz, D$_2$O) δ: 3.69 (dd, J=15, 7 Hz, 1H), 3.76 (s, 2H), 3.84 (dd, J=15, 4 Hz 1H), 3.94–4.03 (m, 3H), 5.72 (ddt, J=25, 7, 2 Hz, 1H), 5.98 (dtd, J=1, 6, 25 Hz, 1H); MS(DCl) m/e 175 (m+H)$^+$, 160, 117, 103, 80; HRMS (DCl) calc'd for C$_6$H$_{15}$N$_4$O$_2$: m/e 175.1195, found: 175.1190; 175(m+H)$^+$.

EXAMPLE 9

3-(1,1-Dimethylethyl)-(S)-4-(3-N$^G$-methylguanidino-orooen-1,E-yl)-2,2-dimethyl-3-oxazolidinecarboxylate To a solution of 3-(1,1-dimethylethyl)-(S)-4-(3-amino-propen-1,E-yl)-2,2 -dimethyl-3-oxazolidinecarboxylate from Example 1h (0.2083 g) in EtOH/H$_2$O 1/1 (9 mL) was added N,S-dimethyl-pseudothiouronium sulfate salt (2.0 eq) and TEA (1.33 eq) and the reaction was stirred at rt for 24 hr. The mixture was concentrated in vacuo. The residue was purified on silica gel and eluted with CH$_3$CN/HOAc/H$_2$O 12/1/1. The material was a colorless oil and was obtained in 17%.: $R_F$0.65(CH$_3$CN/HOAc/H$_2$O 12/1/1); $[\alpha]_D^{20}$=+39.3(c=0.21,MeOH); $^1$H NMR (300 MHz, CD$_3$OD) δ: 1.47 (s, 9H), 1.51 (s, 3H), 1.60 (s, 3H), 2.83 (s, 3H), 3.57 (m, 2H), 3.60 (m, 1H), 3.82 (d, 1H, J=3.5 Hz), 4.08 (m, 1H), 5.70 (m, 2H); MS(FAB/MAT90) m/e 313 (M+H$^+$); Analysis calc'd for C$_{15}$H$_{28}$N$_4$O$_3$: C, 57.66; H, 9.03; N, 17.93; Found: C, 57.31; H, 8.92; N, 17.84.

EXAMPLE 10

N$^G$-Methylguanidinyl-4(S)-Amino-pent-2,E-ene-5-ol

To a solution of 3-(1,1-dimethylethyl)-(S)-4-(3-N$^G$-methylguanidinopropen-1,E-yl)- 2,2-di methyl-3-oxazolidinecarboxylate from Example 9 (0.0889 g) in CH$_2$Cl$_2$ (10 mL) at rt was added TFA (2.0 mL) and the reaction mixture was stirred at rt for 1 hr and concentrated in vacuo. The residue was purified on silica gel and eluted with CH$_3$CN/H$_2$O/HOAc 3/1/1. The product was a yellow oil/foam and was obtained in 61% yield: $R_F$ 0.15 (CH$_3$CN/H$_2$O/HOAc 3/1/1); $^1$H NMR (300 MHz, CD$_3$OD)δ: 2.83 (s, 3H), 3.60 (m, 2H), 3.68 (m, 2H), 3.87 (d, 1H, J=6.5 Hz), 5.23 (dd, 1H, J=15.5, 6.0 Hz), 5.92 (dt, 1H, J=16.5 Hz); $^{13}$NMR (75 MHz, CD$_3$OD) δ: 28.2, 43.3, 55.5, 63.2, 127.4, 132.4, 158.4; MS(FAB/MAT90) m/e 173 (m+H$^+$); $[\alpha]_D^{20}$26.20° (c=1.32, MeOH); Analysis calc'd for C$_7$H$_{16}$N$_4$O.3.0 TFA: C, 30.36; H, 3.72; N, 10.89; Found: C, 30.72; H, 3.40; N, 10.74.

Alternately, to a solution of 3-(1,1-dimethylethyl)-(S)-4-(3-N$^G$ -methylguanidinopropen-1,E-yl)-2,2-dimethyl-3-oxazolidinecarboxylate from Example 9 (0.5784 g) in CH$_2$Cl$_2$ (15 mL) with 0.5 mL of CH$_3$OH was added TFA (2.0 eq) and the reaction mixture was stirred at rt for 1.5 hr under a N$_2$ atmosphere. The mixture was concentrated in vacuo. The residue was purified on amberlite CG-120 and eluted with 1.0 N HCl up to 4.5 N HCl. The material was a yellow oil and was obtained in 71%: $R_F$ 0.30 (CH$_3$CN/HOAc/H$_2$O 3/1/1); $^1$H NMR (300 MHz, D2O) δ: 2.83 (s, 3H), 3.68 (dd, 1H, J=15.0, 9.0 Hz), 3.82 (dd, 1H, J=14.0, 6.0 Hz), 3.90 (d, 1H, J=4.5 Hz), 3.95 (m, 2H), 5.75 (m, 1H), 5.95 (dt, $^1$H, J=14.0, 5.0 Hz); $^{13}$C NMR (75 MHz, D$_2$O) δ: 30.4, 44.7, 56.8, 64.2, 126.7, 135.0, 159.3; MS(FAB/MAT90) m/e 173 ( m+H$^+$); $[\alpha]_D^{20}$=+9.72° (c=1.65, H$_2$O); Analysis calc'd for C$_7$H$_{16}$N$_4$O.4.0 HCl: C, 26.43; H, 6.33; N, 17.61; Found C, 26.17; H, 5.97; N, 17.41.

EXAMPLE 11

3-(1,1-Dimethylethyl)-(S)-4-(3-N$^G$-ethylguanidino-propen-1,E-yl)-2,2-dimethyl-3 -oxazolidinecarboxylate To a solution of 3-(1,1-dimethylethyl)-(S)-4-( 3-amino-propen- 1,E-yl)-2,2-dimethyl-3-oxazolidinecarboxylate from Example 1h (0.4293 g) in EtOH/H$_2$O 1/1 (6 mL) was added N-ethylamidine-2-sulfonic acid (1.1 eq) and potassium carbonate (1.1 eq) and the reaction was stirred at rt for 24 hr. The reaction mixture pH was adjusted to 12–14 and extracted with CH$_2$Cl$_2$ and concentrated in vacuo. The residue was purified on silica gel and eluted with CH$_3$CN/H$_2$O/HOAc 12/1/1. The material was a yellow oil and obtained in 82% yield.: $R_F$ 0.40 (CH$_3$CN/HOAc/H$_2$O 12/1/1); $[\alpha]_D^{20}$=+18.0 (c=0.10, MeOH); $^1$H NMR (300 MHz, CDCl$_3$) δ: 1.18 (t, 3H, J=9.0 Hz), 1.48 (s, 9H), 1.51 (s, 3H), 1.58 (s, 3H), 3.15 (m, 2H), 3.72 (m, 2H), 4.05 (dd, 1H, J=16.0, 8.0 Hz), 4.35 (m, 2H), 5.67 (m, 2H); MS(FAB/MAT90) m/e 327 (m+H$^+$); Analysis calc'd for C$_{16}$H$_{30}$N$_4$O$_3$.0.5 HOAc: C, 57.28; H, 9.04; N, 15.71; Found: C, 57.39; H, 9.04; N, 16.00.

EXAMPLE 12

N$^G$Ethylguanidinyl-4(S)-Amino-pent-2,E-ene-5-ol

To a solution of 3-(1,1-dimethylethyl)-(S)-4-(3-NG-ethylguanidinopropen-1,E-yl)-2,2-dimethyl-3-oxazolidinecarboxylate from Example 11 (0.57 g) in CH$_2$Cl$_2$ (15 mL) was added TFA (2.0 eq) and 0.5 mL of H$_2$O. The reaction mixture was stirred at rt for 2–3 hr. The reaction was concentrated/n vacuo. The residue was purified on silica gel and eluted with CH$_3$CN/H$_2$O/HOAc 3/1/1. The product was a brown oil and obtained in 26% yield: $R_F$ 0.30 (CH$_3$CN/H$_2$O/HOAc 3/1/1); $[\alpha]_D^{20}$=21.26° (c=0.80, H$_2$O). $^1$H NMR (300 MHz, CD$_3$OD)δ: 1.23 (t, 3H, J=9.0 Hz), 3.24 (m, 2H), 3.57 (m, 3H), 3.71 (dd, 1H, J=11.0, 5.0 Hz), 3.85 (d, 1H, J=4.7 Hz), 5.72 (dt, 1H, J=16.0, 10.0 Hz), 5.90 (dt, 1H, J=15.5, 9.0 Hz); MS(FAB/MAT90) m/e 187 (m+H$^+$); Analysis calc'd for C$_8$H$_{18}$N$_4$O: C, 51.58; H, 9.74; N, 30.08; Found: C, 47.17; H, 8.50; N, 16.14.

EXAMPLE 13

$N^4$-Boc-$N^G$-Nitroguanidinyl-4(S)-amino-pent-2,E-ene-5-ol

To a solution of the guanidine from Example 2 (12.0 mmol) at ambient temperature under a $N_2$ atmosphere was added TEA (2 eq) and di-t-butyl-dicarbonate (1.5 eq). The solution was stirred at ambient temperature for 4 hr following by tlc. The reaction was extracted with EtOAc and the combined organic extracts washed with $H_2O$ and brine, dried over $MgSO_4$ and concentrated in vacuo. Purification by flash chromatography eluting with $CH_2Cl_2$/MeOH (2:1) afforded the product as a colorless oil (51%): $R_F$ 0.20 (2:1 $CH_2Cl_2$.MeOH); MS(DCl) m/e 259 (m+H)$^+$.

EXAMPLE 14

3-(1,1-Dimethylethyl)-(S)-4-(3-nitroguanidino-2-methyl-propen-1,E-yl)-2,2-dimethyl-3-oxazolidinecarboxylate Step 14a. 3-(1,1-Dimethylethyl)-(S)-4-(3-(2-methylethoxypropen-2E-oyl))-2.2-dimethyl-3-oxazolidinecarboxylate To a solution of the aldehyde from step 1c (1.70 mmoles) in THF (50 mL) at rt under a $N_2$ atmosphere was added (carbethoxy-ethylidene)triphenyl-phosphorane (2.0 mmoles) and the reaction was stirred at rt for 24 hr. The reaction was concentrated in vacuo and the material was taken up in hexane and the triphenyl phosphine oxide was filtered off and concentrated in vacuo once again to give a yellow oil. The material was purified via flash chromatography with hexane/EtOAc 1/1. This resulted in a 84% yield of a colorless oil.: $R_F$ 0.70 (hexane/EtOAc 1/1); $^1$H NMR(300 MHz, CDCl$_3$) δ1.30 (t, J=7 Hz, 3H), 1.42 (s, 9H), 1.49 (s, 3H), 1.57 (s, 3H), 1.65 (s, 3H), 1.90 (d, J=12 Hz, 2H), 3.70 (dd, J=6, 11 Hz, 1H), 4.12 (m, 1H), 4.21 (m, 2H), 4.60 (m, 1H), 6.65 (m, 1H); $^{13}$C NMR (75 MHz, CDCl$_3$) δ: 12.5, 14.2, 24.4, 25.0, 26.4, 27.3, 28.3, 55.4, 60.6, 67.8, 140.4, 167.6; MS(DCl/NH$_3$) m/e 314 (m+H$^+$), 331 (m+NH$_4^+$); Analysis calc'd for $C_{16}H_{27}NO_5$: C, 61.32; H, 8.68; N, 4.46; found: C, 61.53; H, 8.85; N, 4.32.

Step 14b. 3-(1,1-Dimethylethyl)-(S)-4-(3-hydroxy-2-methylpropen-1,E-yl)-2,2-dimethyl-3-oxazolidinecarboxylate.

To a solution of the enoate from step 14a (0.60 mmoles) in toluene (65 mL) cooled to −78° C. under a $N_2$ atmosphere was added DIBAL (3.10 mmoles) over a 10 minute period while maintaining the temperature below −70° C. The reaction was stirred at −78° C. for 1.5 hr and quenched with MeOH. The reaction was poured into 1M Rochelle salt and stirred for 30 minutes and allowed to separate. The organic layer was poured off, washed with brine and dried over $Na_2SO_4$. The material was concentrated in vacuo and purified on $SiO_2$ with EtOAc/hexane 1/1. A 74% yield of colorless oil product was obtained.: $R_F$ 0.40 (EtOAc/hexane 1/1); $^1$H NMR(300 MHz, CDCl$_3$) δ: 1.45 (s, 9H), 1.53 (s, 3H), 1.60 (s, 3H), 1.74 (s, 3H), 3.67 (dd, J=4.5, 10.25 Hz, 1H), 4.04 (s, 2H), 4.08 (dd, J=7, 12 Hz, 1H), 4.62 (m, 1H), 5.48 (d, J=9.5 Hz, 1H); MS(DCl/NH$_3$) m/e 272 (m+H$^+$), 289 (m+NH$_4^+$); Analysis calc'd for $C_{14}H_{25}NO_4$: C, 61.96; H, 9.28; N, 5.16; found: C, 62.18; H, 9.36; N, 5.08.

Step 14c. 3-(1,1-Dimethylethyl)-(S)-4-(3-phthalimido-2-methyl-propen-1,E-yl)-2,2-dimethyl-3-oxazolidinecarboxylate To a solution of the mesylate (0.30 mmoles) (prepared from the alcohol in step 14b in a manner consistent with step 1f) in DMF (20 mL) under a $N_2$ atmosphere was added potassium phthalimide (1.10 mmoles) and the reaction was warmed to 80° C. for 12 hr. The reaction was poured into EtOAc and washed with $H_2O$ (50 mL) and brine (30 mL) and dried over $NaSO_4$. The organic extract was concentrated in vacuo and purified on SiO2 with hexane/EtOAc 1/1. The product was a colorless oil and was obtained in 69% yield: $R_F$ 0.60 (EtOAc/hexane 1/1); $^1$H NMR(300 MHz, CDCl$_3$) δ: 1.42 (s, 9H), 1.51 (s, 3H), 1.58 (s, 3H), 1.73 (s, 3H), 3.65 (dd, J=6, 12 Hz, 1H), 4.02 (m, 1H), 4.22 (m, 2H), 4.55 (m, 1H), 5.42 (bs, 1H), 7.73 (m, 2H), 7.86 (m, 2H); MS(FAB) m/e 401 (m+H$^+$); Analysis calc'd for $C_{22}H_{28}N_2O_5$: C, 65.98; H, 7.04; N, 6.99; found: C, 65.77; H, 6.87; N 6.80.

Step 14d. 3-(1,1-Dimethylethyl)-(S)-4-(3-amino-2-methylpropen-1,E-yl)-2,2-dimethyl-3-oxazolidinecarboxylate.

To a solution of the phthalimide from step 14c (0.10 mmoles) in MeOH (4.0 mL) at rt under a $N_2$ atmosphere was added 85% hydrazine and the reaction was warmed to 40° C. for 24 hr. The reaction was then poured into brine and washed (3×) with 25 mL of $CH_2Cl_2$, dried over $Na_2SO_4$, and concentrated in vacuo. The material was purified on $SiO_2$ with EtOAc/hexane 1/1. The product was a white solid and was obtained in 81% yield: $R_F$ 0.30 (EtOAc/hexane 1/1); 1H NMR(300 MHz, CDCl$_3$) δ: 1.45 (s, 9H), 1.52 (s, 3H), 1.61 (s, 3H), 1.75 (s, 3H), 3.22 (s, 2H), 3.65 (dd, J=4.5, 9 Hz, 1H), 4.05 (dd, J=7, 13 Hz, 1H), 4.60 (m, 1H), 5.36 (d, J=9.5 Hz, 1H); MS(FAB/MAT) m/e 271 (m+H$^+$); Analysis calc'd for $C_{14}H_{26}N_2O_3$: C, 62.19; H, 9.67; N, 10.36; found: C, 61.87; H, 9.40; N, 10.09.

Step 14e. 3-(1,1-Dimethylethyl)-(S)-4-(3-nitroguanidino-2-methyl-propen-1,E-yl)-2,2-dimethyl-3-oxazolidinecarboxylate.

To a solution of the amine (0.1258 g) from example 14d in EtOH/H$_2$O1/1 6 mL was added the N-nitroS-methylthiopseudourea (1.0 eq), TEA (1.0 eq) and the reaction was stirred at rt for 24 hr. The reaction mixture was concentrated in vacuo. The residue was purified on $SiO_2$ and eluted with $CH_3CN/HOAc/H_2O$ 12/1/1. The material was a colorless oil obtained in 47% yield: $R_F$ 0.60 ($CH_3CN/HOAc/H_2O$ 12/1/1); $^1$H NMR(300 MHz, CD$_3$OD) δ: 1.45 (s, 9H), 1.54 (s, 3H), 1.59 (s, 3H), 1.75 (s, 3H), 3.63 (dd, 1H, J=11.1, 2.0 Hz), 3.71 (s, 2H), 4.10 (dd, 1H, J=15.0, 4.5 Hz), 4.65 (m, 1H), 5.40 (m, 1H); MS(FAB/MAT90) m/e 358 (m +H$^+$); $[α]_D^{20}$= +49.62° (c=1.0, MeOH); Analysis calc'd for $C_{15}H_{27}N_5O_5$.0.10 HOAc: Calc: C, 50.24; H, 7.60; N, 19.27; Found: C, 49.90; H, 7.99; N, 19.00.

EXAMPLE 15

$N^G$-Nitroguanidinyl-4(S)-Amino-2-methyl-pent-2,E-ene-5-ol

Utilizing 3-(1,1-Dimethylethyl)-(S)-4-(3-nitroguanidino-2-methyl-propen-1E-yl)-2,2-dimethyl-3-oxazolidinecarboxylate from Example 14e and the procedure described in Example 2, the title compound was prepared. To a solution of 3-(1,1-Dimethylethyl)-(S)-4-(3-nitroguanidino-2-methylpropen-1,E-yl)-2,2-dimethyl-3-oxazolidinecarboxylate from Example 14e in a solution of $CH_2Cl_2$ (8.0 mL) under a $N_2$ atmosphere was added TFA (2.0 eq) and the reaction mixture was stirred at rt for 2 hr. The mixture was concentrated in vacuo. The residue was purified on silica gel and eluted with $CH_3CN/HOAc/H_2O$ 3/1/1. The material was a yellow oil and was obtained 46%: $R_R$ 0.06 ($CH_3CN/H_2O$/HOAc 3/1/1); $[α]_D^{20}$=+25.0 (c=0.10, MeOH). $^1$H NMR (300 MHz, D$_2$O) δ: 1.80 (s, 3H), 3.65 (dd, 1H, J=14.5, 9.0 Hz), 3.75 (dd, 1H, J= 12.0, 5.0 Hz), 3.92 (s, 2H), 4.25 (m, 1H), 5.32 (d, 1H, J=9.0 Hz); MS(FAB/MAT95) m/e 218 (m+H$^+$).

EXAMPLE 16

3-(1,1-Dimethylethyl)-(S)-4-(3-nitroguanidino-2-benzyl-propen-1,E-yl)-2,2-2,2 -dimethyl-3-oxazolidinecarboxylate Step 16a. 3-(1,1-Dimethylethyl)-(S)-4-(3-(2-benzyl-benzyloxypropen-2E-oyl)- 2,2-dimethyl-3-oxazolidinecarboxylate To a solution of the aldehyde from step 1c (1.50 mmoles) in THF (75 mL) at rt was added (carbobenzyloxy-benzylmethylidene)triphenylphosphorane (1.60 mmoles) and the reaction was stirred at rt for 24 hr under a N$_2$ atmosphere. The reaction was not complete after 24 hr, 1.6 mmoles of the phosphorane was added and the reaction was stirred for an additional 72 hr. The reaction was then concentrated in vacuo to give a yellow oily solid. The reaction mixture was solubilized in hexane and the triphenyl phosphine was removed by filtration. The reaction was purified on SiO$_2$ and eluted with EtOAc/hexane 1/1. The reaction produced a yellow oil in 27% yield: R$_F$ 0.75 (EtOAc/hexane 1/1 ); [α]$_D^{20}$=+29.42 (c=0.65, MeOH). $^1$H NMR(300 MHz, CDCl$_3$) δ: 1.38 (s, 9H), 1.48 (s, 3H), 1.54 (s, 3H), 1.54 (s, 3H), 2.69 (t, J=7 Hz, 2H), 2.98 (t, J=7.5 Hz, 2H), 3.57 (dd, J=4, 9.75 Hz, 1H), 3.82 (dd, J=7, 12 Hz, 1H), 5.15 (m, 2H), 7.25 (m, 10H); MS(FAB/MAT90) m/e 452 (m+H$^+$); Analysis calc'd for C$_{27}$H$_{33}$NO$_5$: C, 71.81;H, 7.36; N, 3.10; found: C, 71.52;H, 7.25; N, 2.87.

Step 16b. 3-(1,1-Dimethylethyl)-(S)-4-(3-hydroxy-2-benzyl-propen-1,E-yl)-2,2 -dimethyl-3-oxazolidinecarboxylate.

To a solution of the enoate from step 16a (0.50 mmoles) in toluene (25 mL) cooled to –78 20 C. under N$_2$ atmosphere was added DIBAL (1M in toluene) over a 10 minute period. The reaction was stirred at –78° C. for 2 hr and quenched with MeOH. The reaction mixture was poured into 1M Rochelle salt and stirred for 30 minutes and allowed to separate. The organic layer was poured off and washed with brine and dried over NaSO$_4$. The solvent was evaporated to yield a yellow oil. The residue was purified on SiO$_2$ and eluted with EtOAc/hexane 1/1 which gave a 62% yeild of a colorless oil: R$_F$ 0.55 (EtOAc/hexane 1/1); [α]$_D^{20}$=+51.68 (c=1.28, CH$_2$Cl$_2$); $^1$H NMR(300 MHz, CDCl$_3$) δ: 1.45 (s, 9H), 1.48 (s, 3H), 1.61 (s, 3H), 3.58 (s, 2H), 4.01 (s, 2H), 4.34 (dd, J=4.5, 8 Hz, 1H), 44.5, (dd, J=5,9 Hz, 1H), 4.62 (bs, 1H), 5.60 (d, J=9.25 Hz, 1H), 7.28 (m, 5H); MS(DCl/ NH$_3$) m/e 348 (m+H$^+$), 365 (m+NH$_4^+$); Analysis calc'd for C$_{20}$H$_{29}$NO$_4$: C, 69.13;H, 8.41; N, 4.03; found: C, 68.90;H, 8.24; N, 4.35.

Step 16c. 3-(1,1-Dimethylethyl)-(S)-4-(3-phthalimido-2-benzyl-propen-1,E-yl)-2,2-dimethyl-3-oxazolidinecarbonxylate, To a solution of the mesylate (prepared from the alcohol in step 16b by a manner similar to step 1f) (0.20 mmoles) in DMF (10mL) was added the potassium phthalimide and the reaction was heated at 80° C. for 24 hr under a N$_2$ atmosphere. The mixture was poured into CH$_2$Cl$_2$ and washed with H$_2$O (50 mL), brine (50 mL), dried over Na$_2$SO$_4$, and concentrated in vacuo. The material was purified on SiO$_2$ and eluted with EtOAc/hexane 1/1 to give a 57% yield of a colorless oil: R$_F$ 0.70 (EtOAc/hexane 1/1); [α]=+$_D^{20}$ 21.26 (c=0.41, MeOH), $^1$H NMR(300 MHz, CDCl$_3$) δ: 1.41 (s, 9H), 1.50 (s, 3H), 1.58 (s, 3H), 3.75 (m, 1H), 4.01 (dd, J=7, 15.5 Hz, 1H), 4.23 (m, 2H), 4.63 (bs, 1H), 4.86 (s, 2H), 5.66 (d, J=9.5 Hz, 1H), 7.30 (m, 3H), 7.95 (m, 2H), 7.71 (m, 2H), 7.87 (m, 2H); MS(FAB/MAT90) m/e 477 (m+H$^+$); Analysis calc'd for C$_{28}$H$_{32}$N$_2$O$_5$: C, 70.56; H, 6.76; N, 5.87; found: C, 70.37;H, 6.42; N, 5.78.

Step 16d. 3-(1,1-Dimethylethyl)-(S)-4-(3-amino-2-benzyl-propen-1,E-yl)-2,2 -dimethyl-3-oxazolidinecarboxylate.

To a solution of the phthalimide from step 16c (0.10 mmoles) in MeOH (15 mL) was added 85% hydrazine and the reaction was warmed to 40° C. for 24 hr under a N$_2$ atmosphere. The reaction was poured into brine (100 mL) and extracted with Et$_2$O (4×, 50 mL). The organic layer was dried over Na$_2$SO$_4$ and concentrated in vacuo. The material was purified on SiO$_2$ and eluted with MeOH containing 2% NH$_4$OH. This gave a 67% yield of a colorless oil. R$_F$=0.50 (MeOH with 2% NH$_4$OH); [α]$_D^{20}$=+41.82 (c=1.26, MeOH); $^1$H NMR(300 MHz, (300 MHz, CDCl$_3$) δ: 1.45 (s, 9H), 1.51 (s, 3H), 1.63 (s, 3H), 3.20 (s, 2H), 3.68 (dd, J=4.5, 12.3 Hz, 1H), 3.77 (d, J=15 Hz, 2H), 3.98 (m, 1H), 4.71 (bs, 1H), 5.58 (d, J=10 Hz, 1H), 7.18 (m, 3H), 7.28 (m, 2H); MS(FAB/ MAT90) m/e 347 (m+H$^+$). Analysis calc'd for C$_2$H$_{30}$N$_2$O$_3$.0.3 MeOH: C, 68.47;H, 8.83; N, 7.86; Found: C, 68.11;H, 8.44; N, 7.43.

Step 16e. 3-(1,1-Dimethylethyl)-(S)-4-(3-nitroguanidino-2-benzyl-propen-1,E-yl)-2,2-dimethyl-3-oxazolidinecarboxylate.

Using the method of example 1i and the product of example 16d as starting material the product is prepared.

EXAMPLE 17

N$^4$, Boc-N$^G$-Methylguanidinyl-4(S)-Amino-pent-2,E-ene-5-ol

To a solution of 3-(1,1-dimethylethyl)-(S)-4-(3-aminopropen-1,E-yl)-2,2 -dimethyl-3-oxazolidinecarboxylate from Example 1h (1.0 eq) in EtOH/H$_2$O 1/1 (9.0 mL) was added N-methyl-S-methylthiopseudouronium sulfate (2.0 eq) and TEA (1.0 eq) and the reaction mixture was stirred at rt for 24 hr. The reaction mixture was concentrated in vacuo. The residue was purified on silica gel and eluted with CH$_3$CN/HOAc/H$_2$O 12/1/1. In addition to the product N$^G$-Methylguanidinyl-4(S)-Amino-pent-2,E-ene-5-ol (cf. Example 10) the title product was obtained in 12% yield as a white oil: R$_F$0.50 (CH$_3$CN/HOAc/H$_2$O 12/1/1 ); $^1$H NMR (300 MHz, CD$_{OD3}$OD) δ: 1.49 (s, 9H), 2.85 (s, 3H), 3.60 (m, 2H), 3.62 (m, $^1$H), 3.85 (d, 1H, J=3.8 Hz), 4.12 (m, 1H), 5.72 (m, 2H); MS(FAB/MAT90) m/e 273 (m+H$^+$); Analysis calc'd for C$_{12}$H$_{24}$N$_4$O$_3$.1.0 HOAc: Calc: C, 50.58; H 8.49; N, 16.85; Found: C, 50.32;H, 8.13; N, 16.79.

EXAMPLE 18

3-(1,1-Dimethylethyl)-(R)-4-(3-N$^G$-methylguanidinopropen-1,E-yl)-2,2-dimethyl-3 -oxazolidinecarboxylate Utilizing 3-(1,1-dimethylethyl)-(R)-4-(3-aminopropen-1, E-yl)-2,2-dimethyl-3-oxazolidinecarboxylate prepared in an analogous manner to its enantiomer from Example 1h and N,S-dimethyl-pseudothiouronium sulfate salt, the title compound is prepared using the procedure described in Example 1g. To a solution of 3-(1,1-dimethylethyl)-(R)-4-(3-aminopropen-1,E-yl)-2,2-dimethyl-3-oxazolidinecarboxylate prepared in an analogous manner to its enantiomer from Example 1h (0.1965 g) in EtOH/H$_2$O (4/1) (1.0M) was added N,S-dimethyl-pseudothiouronium sulfate salt (1.1 eq) and TEA (1.1 eq) and the reaction mixture was stirred at rt for 48 hr. The mixture was concentrated in vacuo. The residue was purified on silica gel and eluted with $CH_3CN/HOAc/H_2O$ (12/1/1). The material was not pure so another silica gel column was run with elution with $CH_2Cl_2/CH_3OH$ (3/1). The material was a colorless oil and obtained in 62% yield: $R_F$ 0.70 ($CH_3CN/HOAc/H_2O$ 12/1/1/1); $[\alpha]_D^{20}=-44.9$ (c=0.76, MeOH); $^1$H NMR (300 MHz, $CD_3OD$) δ: 1.48 (s, 9H), 1.50 (s, 3H), 1.58 (s, 3H), 2.75 (s, 3H), 3.53 (m, 2H), 3.72 (dd, 1H, J=12.0, 5.0 Hz), 3.85 (d, 1H, J=4.5 Hz), 4.10 (dd, 1H, J=14.5, 7.0 Hz), 5.65 (m, 2H); MS (FAB/MAT90) m/e 313 (m+H$^+$); Analysis calc'd for $C_{15}H_{28}N_4O_3.3.0$ $CH_2Cl_2$: C, 38.11;H, 6.04; N, 9.87; Found: C, 38.35;H, 6.03; N, 9.88.

EXAMPLE 19

N-$^G$-Methylguanidinyl-4(R)-Amino-pent-2,E-ene,5-ol

To a solution of 3-(1,1-dimethylethyl)-(R)-4-(3-N$^G$-methylguanidinopropen-1,E-yl)-2,2-dimethyl-3-oxazolidinecarboxylate from Example 18 (2.0 mg) in $CH_2Cl_2$ was added 0.10 mL of TFA and one drop of $H_2O$. When the reaction did not appear to proceed by tlc 4N HCl (2 mL) was added. The reaction mixture was stirred for 1 hr and concentrated in vacuo. The material residue was purified over silica gel and eluted with $CH_2Cl_2/MeOH$ (3/1) with 5% HOAc. Product yield was 18%: $R_F$ 0.25 ($CH_2Cl_2/MeOH$ (3/1, with 5% HOAc); $^1$H NMR(300 MHz, $CD_3OD$) δ: 2.82 (s, 3H), 3.55 (m, 2H), 3.70 (m, 2H), 3.85 (d, 1H J=7.5 Hz), 5.25 (m, 1H), 5.85 (m, 1H); $^{13}$C NMR (75 MHz, $CD_3OD$) δ: 28.2, 43.3, 55.5, 63.2, 127.0, 132.4, 158.4; MS(FAB/MAT90) m/e 173 (m+H$^+$); $[\alpha]_D^{20}=-12.62°$ (c=0.60, MeOH); Analysis calc'd for $C_7H_{16}N_4O.3.2$ HOAc: C, 44.16;H, 7.96; N, 15.39; Found: C, 43.92;H, 7.68; N, 15.16.

EXAMPLE 20

3-(1,1-Dimethylethyl)-(S)-4-(3-guanidino-2-methyl-propen-1,E-yl)-2,2-dimethyl-3-oxazolidinecarboxylate To a solution of 3-(1,1-Dimethylethyl)-(S)-4-(3-amino-2-methylopropen-1,E-yl)-2,2-dimethyl-3-oxazolidinecarboxylate from step 14d (0.1253 g) in $EtOH/H_2O$ 1/1 10 mL was added N,S-dimethyl-pseudothiouronium sulfate salt (1.0 eq), TEA (1.0 eq) and the reaction was stirred at rt for 48 hr. The reaction was concentrated in vacuo. The product was purified on silica gel and eluted with acetonitrile/MeOH 1/1 with 0.5% HOAc. The material was a colorless oil and obtained in 64%: $R_F$ 0.30 ($CH_3CN/HOAc/H_2O$ 12/1/1); 1H NMR(300 MHz, $CD_3OD$) δ: 1.46 (s, 9H), 1.50 (s, 3H), 1.57 (s, 3H), 1.75 (s, 3H), 3.63 (dd, 1H, J=2.4, 8.7 Hz), 3.72 (s, 2H), 4.12 (dd, 1H, J=6.8.7 Hz), 4.65 (m, 1H), 5.40 (m, 1H); MS(FAB/MAT90) m/e 313 (m+H$^+$); $[\alpha]_D^{20}=+62.00°$ (c=1.00, MeOH); Analysis calc'd for $C_{15}H_{28}N_4O_3.0.10$ HOAc: C, 51.78;H, 8.26; N, 11.95; Found: C, 51.38; H, 8.50; N, 11.99.

EXAMPLE 21

N$^G$-Guanidinyl-4(S)-Amino-2-methyl-pent-2,E-ene-5-ol

To a solution of 3-(1,1-Dimethylethyl)-(S)-4-(3-guanidino-2-methyl-propen-1,E-yl)-2,2-dimethyl-3-oxazolidinecarboxylate from Example 20 (.0698 g) in $CH_2Cl_2$ 10 mL was added 5.0 mL of TFA and 0.10 mL of $H_2O$. The reaction was stirred at rt for 1.5 hr. The reaction was concentrated/n vacuo. The residue was purified on silica gel and eluted with $CH_3CN/HOAc/H_2O$ 3/1/1. The product was a white solid and obtained in 84% yield: $R_F$ 0.20 ($CH_3CN/HOAc/H_2O$ 3/1/1); $^1$H NMR(300 MHz, $D_2O$) δ1.78 (s, 3H), 3.62 (dd J=5.5, 9 Hz,, 1H), 3.72 (dd, J=5, 8 Hz, 1H), 3.83 (s, 2H), 4.25 (m, 1H), 5.28 (dq, J=9.5 Hz, 1H); MS(FAB/MAT90) m/e 173 (m+H$^+$); $[\alpha]_D^{20}=+12.26°$ (c=1.00, $H_2O$); Analysis calc'd for for $C_7H_{16}N_4O.3.20$ HOAc.0.90 $H_2O$: C, 42.29;H, 8.10; N, 14.72; Found: C, 42.27;H, 7.90; N, 14.63.

Example 22

3-(1,1-Dimethylethyl)-(R)-4-(3-guanidinopropen-1.E-yl)-2,2-dimethyl-3 -oxazolidinecarboxylate Utilizing the same procedure outlined in example 3 the enantiomer of example 3 is prepared: To a solution of the enantiomeric R- allylic amine (1.0 eq) in $EtOH/H_2O$ 1/1 was added the S-methyl-pseudothiouronium sulfate (1.0 eq) and TEA (1.0 eq) and the reaction was stirred at rt for 24 hr. The reaction was concentrated in vacuo. The residue was purified on silica gel and eluted with $CH_3CN/MeOH$ (1/1 with 1% HOAc): $R_F$ 0.35 $CH_3CN/MeOH$ (1/1 with 1% HOAc); $^1$H NMR(300 MHz, $CD_3OD$) δ: 1.49 (bs, 12H), 1.56 (s, 3H), 3.73 (dd, J=1.8, 11.4 Hz, 1H), 3.82 (d, 2H, J=3.6 Hz), 4.08 (dd, 1H, J=11.4, 5.7 Hz), 4.37 (m, 1H), 5.66 (m, 2H); $^{13}$C NMR(75 MHz, $CD_3OD$) δ: 23.8, 25.0, 27.0, 27.7, 28.7, 43.1, 59.95, 9.0, 81.95, 95.1, 132.6, 133.5, 158.9; HRMS-(DCI/NH$_3$) calc'd for $C_{14}H_{27}N_4O_3$: m/e 299.2083, found: 299.2071; $[\alpha]_D^{20}=-24.95°$ (c=1.1, MeOH); Analysis calc'd for $C_{14}H_{26}N_4O_3.1.40$ $H_2O.3.3$ HOAc. $1.5CH_3CN$: C, 48.59; H, 8.03; N, 13.21; Found: C, 48.55;H, 7.72; N, 13.16.

EXAMPLE 23

1-Guanidinyl-4(R)-amino-pent-2,E-ene-5-ol

Utilizing the material from example 22 and the procedure of example 4 the product is prepared.

EXAMPLE 24

3-(1,1-Dimethylethyl)-(S)-4-(3,guanidino-2-benzyl-propen-1,E,yl)-2,2-dimethyl--oxazolidinecarboxylate.

To a solution of 3-(1,1-Dimethylethyl)-(S)-4-(3-amino-2-benzyl-propen-1,E-yl)-2,2-dimethyl-3-oxazolidinecarboxylate from example 16d in $EtOH/H_2O$ 1/1 (4 mL) was added S-methyl-pseudothiouronium sulfate salt (1.1 eq) and TEA (2.0 eq) and the reaction was stirred at rt for 72 hr. The reaction was concentrated in vacuo. The material was purified on silica gel and eluted with $CH_2Cl_2/MeOH/HOAc$, (49/49/0.5). The product was a yellow oil obtained in 26% yield: $R_F$ 0.30 ($CH_2Cl_2/MeOH/HOAc$ 49/49/0.5); $[\alpha]_D^{20}=+26.42°$ (c=0.16, MeOH); $^1$H NMR(300 MHz, $CD_3OD$) δ: 1.50 (s, 9H), 1.58 (s, 3H), 1.62 (s, 3H), 3.35 (s, 2H), 3.62 (m, 1H), 4.25 (m, 4H), 4.72 (bs, 1H), 5.63 (m, 1H), 7.25 (m, 5H); MS(FAB/MAT90) m/e 389 (m+H$^+$); Analysis calc'd for $C_{21}H_{32}N_4O_3.3.0$ HOAc: C, 57.02;H, 7.79; N, 9.85; Found: C, 57.24;H, 7.68; N, 9.87.

EXAMPLE 25

N$^G$-Guanidinyl-4(S)-Amino-2-benzyl-pent-2,E-ene-5-ol

To a solution of the material from example 24 (0.0078 g) in $CH_2Cl_2$ (2.0 mL) under a $N_2$ atmosphere was added TFA (1.0 eq) and one drop of $H_2O$ and the reaction was stirred at rt for 1.5 hr. The mixture was concentrated and purified on silica gel and eluted with $CH_3CN/HOAc/H_2O$ 3/1/1. The material was not sufficiently pure so it was further purified on CG-120 amberlite and eluted with 1.0N HCl up to 4.0N HCl. The product was a yellow oil and obtained in 12% yield: $R_f$ 0.30 (CH$_3$CN/H$_2$O /HOAc, 3/1/1); $[\alpha]_D^{20}$=+16.2 (c=0.18, H$_2$O). $^1$H NMR (300 MHz, D$_2$O) δ: 3.60 (s, 2H), 3.65 (m, 1H), 3.75 (m, 1H), 3.82 (s, 2H), 4.00 (m, 1H), 5.65(dd, 1H, J=15.0Hz), 7.35(m, 5H); MS(FAB/MAT95) m/e 249(m+H$^+$); Analysis calc'd for C$_{13}$H$_2$O N$_4$O.6.0 HCl: C, 33.42;H, 5.61; N, 11.99; Found: C, 33.22;H, 5.96; N, 11.70.

EXAMPLE 26

3-(1,1-Dimethylethyl)-(S)-4-(3-N$^G$-methylguanodino-2-methyl-propen-1,E-yl)-2,2-dimethyl-3-oxazolidinecarboxylate Utilizing the material 3-(1,1-Dimethylethyl)-(S)-4-(3-amino-2-methyl-propen-1,E-yl)-2,2-dimethyl-3-oxazolidinecarboxylate from example 14d and the procedure from example 9 the title compound is prepared. $R_f$ 0.30 (CH$_3$CN/H$_2$O/HOAc 12/1/1); $[\alpha]_D^{20}$=+6.81 (c=0.21, MeOH); $^1$H NMR (300 MHz, CD$_3$OD) δ1.48 (s, 9H), 1.50 (s, 3H), 1.56 (s, 3H), 1.92 (s, 3H), 2.85 (s, 3H), 3.52 (m, 1H), 3.75 (s, 2H), 4.10 (dd, J=4, 9 Hz, 1H), 4.40 (m, 1H), 5.35 (d, J=8.5 Hz, 1H); MS(FAB) m/e 327 (m+H$^+$).

EXAMPLE 27

N$^G$-Methylguanidinyl-4(S)-Amino-2-methyl-pent-2,E-ene-5-ol

To a solution of the material from example 26 (0.010 g) in CH$_2$Cl$_2$ (2.0 mL) under a N$_2$ atmosphere was added TFA (1.1 eq) and the reaction mixture was stirred at rt for 2 hr. The mixture was concentrated in vacuo. The residue was purified on ion-exchange CG-120 amberlite and eluted with 1N HCl up to 6N HCl. The material was yellow oil and obtained in 21% yield: $R_f$ 0.35 (CH$_3$CN/HOAc/H$_2$O, 3/1/1 ); $^1$H NMR (300 MHz, D$_2$O), 67 : 1.80 (s, 3H), 2.87 (s, 3H), 3.67 (dd, 1H, J=15.0, 5.25 Hz), 4.04 (s, 2H), 4.12 (dd, 1H, J=11.5, 4.0 Hz), 4.70 (m, 1H), 5.52 (d, 1H, J=4.2 Hz); MS(FAB/MAT95) m/e 187 (m+H$^+$); $[\alpha]_D^{20}$ =+7.28° (c=0.24, H$_2$O); Analysis calc'd for C$_8$H$_{18}$N$_4$O.7.0 HCl: C, 21.76;H, 5.57; N, 12.69; Found C, 21.46; H, 5.37; N, 12.37.

EXAMPLE 28

3-(1,1-Dimethylethyl)-(S)-4-(3-N$^G$propylguanidino-2-methyl-propen-1,E-yl)-2,2-dimethyl-3-oxazolidine-carbonxylate To a solution of 3-(1,1-Dimethylethyl)-(S)-4-(3-amino-2-methyl-propen-1,E-yl)-2,2-dimethyl-3-oxazolidinecarboxylate from example 14d (0.1219 g) in EtOH/H$_2$O (1/1) (10 mL) was added N-propyl-S-methyl-pseudothiouronium hydrochloride salt (1.1 eq) and then K$_2$CO$_3$ (1.1 eq). The reaction was stirred at rt for 48 hr. The reaction was concentrated in vacuo. The product was purified on silica gel and eluted with CH$_3$CN/HOAc/H$_2$O (12/1/1). The product was a colorless oil and obtained in 21% yield: $R_f$ 0.50 (CH$_3$CN/HOAc/H$_2$O, 12/1/1); $[\alpha]_D^{20}$=+31.6 (c=0.28, MeOH); 1H NMR (300 MHz, CD$_3$OD) δ: 0.95 (t, 3H, J=9.5 Hz), 1.48 (s, 9H), 1.51 (s, 3H), 1.58 (s, 3H), 1.62 (m, 2H), 1.75 (s, 3H), 3.17 (t, 2H, J=11.5 Hz), 3.62 (dd, 1H, J=12.0, 6.0 Hz), 3.75 (bs, 2H), 4.11 (dd, 1H, J= 12.0, 6.5 Hz), 4.68 (m, 1H), 5.36 (bs, 1H); MS(FAB/MAT95) m/e 355 (m+H$^+$); Analysis calc'd for C$_{18}$H$_{34}$N$_4$O$_3$: C, 60.98;H, 9.66; N, 15.80; Found C, 60.59;H, 9.42; N, 15.33.

EXAMPLE 29

N-$^G$-Propylguanidinyl-4(S)-Amino-2-methyl-pent-2,E-ene-5-ol

Utilizing the material from example 28 and the procedure from example 4 the title compound is prepared.

The foregoing examples are merely illustrative of the invention and are not intended to limit the invention to the disclosed compounds. Variations and changes which are obvious to one skilled in the art are intended to be within the scope and nature of the invention which is defined in the appended claims.

What is claimed is:

1. A compound of the formula:

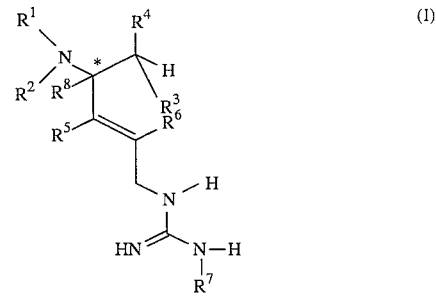

or a pharmaceutically-acceptable salt, ester, amide or prodrug thereof, wherein:

$R^1$ is selected from the group consisting of:
(1) hydrogen;
(2) $C_1$–$C_6$-alkyl;
(3) $C_6$–$C_{12}$-aryl-$C_1$–$C_4$-alkyl;
(4) substituted $C_6$–$C_{12}$-aryl-$C_1$–$C_4$-alkyl;
(5) N-protecting group;
(6) —CO—$C_1$–$C_6$-alkyl;
(7) —CO—$C_6$–$C_{12}$-aryl;
(8) —CO—substituted $C_6$–$C_{12}$-aryl;
(9) —CO—($C_6$–$C_{12}$-aryl-$C_1$–$C_4$-alkyl);
(10) —CO—(substituted $C_6$–$C_{12}$-aryl-$C_1$–$C_4$-alkyl); and
(11) —CO-Het;

$R^2$ is selected from the group consisting of:
(1) hydrogen;
(2) $C_1$–$C_6$-alkyl;
(3) $C_6$–$C_{12}$-aryl-$C_1$–$C_4$-alkyl; and
(4) substituted $C_6$–$C_{12}$-aryl-$C_1$–$C_4$-alkyl;

$R^3$ is selected from the group consisting of:
(1) hydrogen;
(2) $C_1$–$C_6$-alkyl;
(3) $C_2$–$C_6$-alkenyl;
(4) cyclo-$C_3$–$C_7$-alkyl;
(5) $C_6$–$C_{12}$-aryl; and
(6) substituted $C_6$–$C_{12}$-aryl;

$R^4$ is selected from the group consisting of:
(1) hydroxy;
(2) $C_1$–$C_6$-alkoxy;
(3) $C_6$–$C_{12}$-aryloxy;
(4) substituted $C_6$–$C_{12}$-aryloxy;
(5) —O—($C_1$–$C_6$-alkyl-$C_6$–$C_{12}$-aryl);
(6) —O—(substituted $C_6$–$C_{12}$-aryl-$C_1$–$C_4$-alkyl); and
(7) —NHR$^{11}$, wherein R$^{11}$ is hydrogen or $C_1$–$C_4$-alkyl; or $R^2$ and $R^4$ are linked together by a single bond to form a nitrogen-containing ring of the formula:

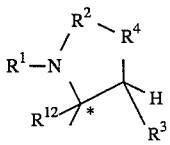

wherein $R^1$ and $R^3$ are as defined above, $R^4$ is O and $R^2$ is —$CR^9R^{10}$, wherein $R^9$ is selected from the group consisting of:
(1) hydrogen;
(2) $C_1$–$C_6$-alkyl;
(3) substituted $C_1$–$C_6$-alkyl;
(4) $C_6$–$C_{12}$-aryl;
(5) substituted $C_6$–$C_{12}$-aryl;
(6) $C_2$–$C_6$-alkenyl;
(7) carboxy;
(8) $C_1$–$C_4$-alkoxycarbonyl, as defined below;
(9) carboxamido; and
(10) cyano;

$R^{10}$ is hydrogen or $C_1$–$C_6$-alkyl; and
$R^{12}$ is hydrogen or $C_1$–$C_4$-alkyl;
$R^5$ and $R^6$ are independently selected from the group consisting of:
(1) hydrogen;
(2) $C_1$–$C_4$-alkyl;
(3) $C_6$–$C_{12}$-aryl-$C_1$–$C_6$-alkyl;
(4) substituted $C_6$–$C_{12}$-aryl-$C_1$–$C_6$-alkyl;
(5) halo-$C_1$–$C_2$-alkyl; and
(6) halogen;

$R^7$ is selected from the group consisting of:
(1) hydrogen;
(2) $C_1$–$C_3$-alkyl;
(3) cyano;
(4) nitro;
(5) hydroxy;
(6) amino; and
(7) —$OR^{15}$, wherein $R^{15}$ is a hydroxy-protecting group;

$R_8$ is hydrogen or $C_1$–$C_4$-alkyl; and * may be a chiral center.

2. A compound according to claim 1, wherein $R^1$, $R^3$, $R^5$, $R^6$, $R^7$ and $R^8$ are as defined above and $R^2$ and $R^4$ are linked together to form a nitrogen-containing ring as defined above.

3. A compound according to claim 2, wherein $R^5$ and $R^6$ are hydrogen and the chiral center is S.

4. A compound according to claim 1, wherein $R^1$, $R^2$, $R^3$, $R^5$, $R^6$, $R^7$, and $R^8$ are as defined above, and $R^4$ is hydroxy.

5. A compound according to claim 4, wherein $R^5$ and $R^6$ are hydrogen and the chiral center is S.

6. A compound according to claim 1, which is:

$N^G$-Nitroguanidinyl-4(S)-amino-pent-2,E-ene-5-ol;
3-(1,1-Dimethylethyl)-(S)-4-(3-guanidinopropen-1,E-yl)-2,2-dimethyl-3-oxazolidinecarboxylate;
1-Guanidinyl-4(S)-amino-pent-2,E-ene-5-ol;
$N^G$-Aminoguanidinyl-4(S)-amino-pent-2,E-ene-5-ol;
3-(1,1-Dimethylethyl)-(S)-4-(3-$N^G$-hydroxyguanidinopropen-1,E-yl)-2,2-dimethyl-3-oxazolidinecarboxylate;
$N^G$-Hydroxyguanidinyl-4(S)-amino-pent-2,E-ene-5-ol;
3-(1,1-Dimethylethyl)-(S)-4-(3-$N^G$-methylguanidinopropen-1,E-yl)-2,2-dimethyl-3-oxazolidinecarboxylate;
$N^G$-Methylguanidinyl-4(S)-amino-pent-2,E-ene-5-ol;
3-(1,1-Dimethylethyl)-(S)-4-(3-$N^G$-ethylguanidinopropen-1,E-yl)-2,2-dimethyl-3-oxazolidinecarboxylate;
$N^G$-Ethylguanidinyl-4(S)-amino-pent-2,E-ene-5-ol;
$N^4$-Boc-$N^G$-Nitroguanidinyl-4(S)-amino-pent-2,E-ene-5-ol;
3-(1,1-Dimethylethyl)-(S)-4-(3-nitroguanidino-2-methyl-propen-1,E-yl)-2,2-dimethyl-3-oxazolidinecarboxylate;
$N^G$-Nitroguanidinyl-4(S)-amino-2-methyl-pent-2,E-ene-5-ol;
$N^4$-Boc-$N^G$-Methylguanidinyl-4(S)-amino-pent-2,E-ene-5-ol;
3-(1,1-Dimethylethyl)-(R)-4-(3-$N^G$-methylguanidinopropen-1,E-yl)-2,2-dimethyl-3-oxazolidinecarboxylate;
$N^G$-Methylguanidinyl-4(R)-amino-pent-2,E-ene-5-ol;
3-(1,1-Dimethylethyl)-(S)-4-(3-methylguanidino-2-methyl-propen-1,E-yl)-2,2-dimethyl-3-oxazolidinecarboxylate;
$N^G$-Methylguanidinyl-4(S)-amino-2-methyl-pent-2,E-ene-5-ol;
3-(1,1-Dimethylethyl)-(R)-4-(3-guanidinopropen-1,E-yl)-2,2-dimethyl-3-oxazolidinecarboxylate;
3-(1,1-Dimethylethyl)-(S)-4-(3-guanidino-2-benzyl-propen-1,E-yl)-2,2-dimethyl-3-oxazolidinecarboxylate;
$N^G$-Guanidinyl-4(S)-amino-2-benzyl-pent-2,E-ene-5-ol;
$N^G$-Methylguanidinyl-4(S)-Amino-2-methyl-pent-2,E-ene-5-ol; or
3-(1,1-Dimethylethyl)-(S)-4-(3-$N^G$-propylguanidino-2-methyl-propen-1,E-yl)-2,2-dimethyl-3-oxazolidinecarboxylate.

7. A compound according to claim 6, which is:
$N^G$-Nitroguanidinyl-4(S)-amino-pent-2,E-ene-5-ol;
$N^G$-Methylguanidinyl-4(S)-amino-pent-2,E-ene-5-ol;
$N^G$-Nitroguanidinyl-4(S)-amino-2-methyl-pent-2,E-ene-5-ol;
$N^G$-Guanidinyl-4(S)-amino-2-methyl-pent-2,E-ene-5-ol; or
$N^G$-Methylguanidinyl-4(S)-amino-2-methyl-pent-2,E-ene-5-ol.

8. A pharmaceutical composition for treating disorders of the vascular system or diseases of the cartilage characterized by the regulation of soluble guanylate cyclase or nitric oxide synthase activity, comprising a pharmaceutically-acceptable carrier and a therapeutically-effective amount of a compound according to claim 1.

* * * * *